(12) United States Patent
Wingeier et al.

(10) Patent No.: US 12,029,894 B2
(45) Date of Patent: Jul. 9, 2024

(54) SYSTEM FOR ELECTRICAL STIMULATION

(71) Applicant: Flow Neuroscience, Inc., Palo Alto, CA (US)

(72) Inventors: Brett Wingeier, San Francisco, CA (US); Ian Shain, San Francisco, CA (US); Colin Davis, San Francisco, CA (US); Victoria Hammett, San Francisco, CA (US); Mardis Bagley, San Francisco, CA (US); Phnam Bagley, San Francisco, CA (US)

(73) Assignee: Flow Neuroscience, Inc., Palo Alto, CA (US)

( * ) Notice: Subject to any disclaimer, the term of this patent is extended or adjusted under 35 U.S.C. 154(b) by 132 days.

(21) Appl. No.: 17/410,868

(22) Filed: Aug. 24, 2021

(65) Prior Publication Data

US 2021/0393946 A1 Dec. 23, 2021

Related U.S. Application Data

(63) Continuation of application No. 16/683,839, filed on Nov. 14, 2019, now Pat. No. 11,191,949, which is a
(Continued)

(51) Int. Cl.
*A61N 1/04* (2006.01)
*A61B 5/00* (2006.01)
(Continued)

(52) U.S. Cl.
CPC ............ *A61N 1/0492* (2013.01); *A61B 5/291* (2021.01); *A61B 5/6803* (2013.01);
(Continued)

(58) Field of Classification Search
CPC ...... A61N 1/04; A61N 1/0412; A61N 1/0424; A61N 1/0428; A61N 1/0452;
(Continued)

(56) References Cited

U.S. PATENT DOCUMENTS

| 3,472,233 A | 10/1969 | Sarbacher |
| 4,928,696 A | 5/1990 | Henderson et al. |

(Continued)

FOREIGN PATENT DOCUMENTS

| CN | 101801445 A | 8/2010 |
| CN | 102083495 A | 6/2011 |

(Continued)

OTHER PUBLICATIONS

US 8,919,831, 07/2011, Tateishi et al. (withdrawn)
(Continued)

*Primary Examiner* — Brian T Gedeon
(74) *Attorney, Agent, or Firm* — COOLEY LLP

(57) ABSTRACT

In an embodiment, an electrical stimulation system can include one or more of an electrode assembly including one or more electrodes and an electronics subsystem. In some variations, each of the one or more electrodes can include a hydrophilic layer and a conductive layer. In some variations, the electronics subsystem can include one or more of a control module, power module, and a stimulus generator. In some variations, the electrical stimulation can further include one or more of an electrical attachment system, mechanical attachment system, head apparel assembly, flexible housing, and/or any other suitable component. The electrical stimulation system functions to apply electrical stimulation but can additionally or alternatively function to measure/and or record one or more biosignals from a user.

20 Claims, 19 Drawing Sheets

Related U.S. Application Data continuation of application No. 15/916,170, filed on Mar. 8, 2018, now Pat. No. 10,525,255.

(60) Provisional application No. 62/526,643, filed on Jun. 29, 2017, provisional application No. 62/486,348, filed on Apr. 17, 2017, provisional application No. 62/468,624, filed on Mar. 8, 2017, provisional application No. 62/468,616, filed on Mar. 8, 2017.

(51) Int. Cl.
  *A61B 5/291* (2021.01)
  *A61N 1/36* (2006.01)
  *A61B 5/24* (2021.01)
  *A61N 1/378* (2006.01)
  *A61N 7/00* (2006.01)

(52) U.S. Cl.
  CPC ........... *A61N 1/0476* (2013.01); *A61N 1/048* (2013.01); *A61N 1/0484* (2013.01); *A61N 1/0496* (2013.01); *A61N 1/36025* (2013.01); *A61B 5/24* (2021.01); *A61N 1/36092* (2013.01); *A61N 1/36096* (2013.01); *A61N 1/3787* (2013.01); *A61N 7/00* (2013.01); *A61N 2007/0026* (2013.01)

(58) Field of Classification Search
  CPC .... A61N 1/0456; A61N 1/046; A61N 1/0464; A61N 1/0468; A61N 1/0492; A61N 1/0526; A61N 1/0529; A61N 1/0531; A61N 1/0534; A61N 1/0536; A61N 1/36014; A61N 1/36021; A61N 1/36025; A61N 1/36028; A61N 1/36064; A61N 1/36067; A61N 1/36071; A61N 1/36075
  See application file for complete search history.

(56) References Cited

U.S. PATENT DOCUMENTS

| | | | |
|---|---|---|---|
| 4,967,038 A | 10/1990 | Gevins et al. |
| 4,977,895 A | 12/1990 | Tannenbaum |
| 5,058,605 A | 10/1991 | Slovak |
| 5,087,242 A | 2/1992 | Petelenz et al. |
| 5,137,817 A | 8/1992 | Busta et al. |
| 5,250,023 A | 10/1993 | Lee et al. |
| 5,387,231 A | 2/1995 | Sporer |
| 5,622,168 A | 4/1997 | Keusch et al. |
| 6,026,327 A | 2/2000 | Dervieux |
| 6,077,237 A | 6/2000 | Campbell et al. |
| 6,263,226 B1 | 7/2001 | Axelgaard et al. |
| 6,379,324 B1 | 4/2002 | Gartstein et al. |
| 6,406,811 B1 | 6/2002 | Hall et al. |
| 6,480,743 B1 | 11/2002 | Kirkpatrick et al. |
| 6,505,079 B1 | 1/2003 | Foster et al. |
| 6,510,333 B1 | 1/2003 | Licata et al. |
| 6,574,513 B1 | 6/2003 | Collura et al. |
| 7,024,247 B2 | 4/2006 | Gliner et al. |
| 7,551,952 B2 | 6/2009 | Gevins et al. |
| 7,610,095 B2 | 10/2009 | Naisberg |
| 7,813,802 B2 | 10/2010 | Tcheng et al. |
| 7,818,515 B1 | 10/2010 | Umbehocker et al. |
| 7,828,947 B2 | 11/2010 | Oki et al. |
| 7,877,146 B2 | 1/2011 | Ansarinia et al. |
| 7,894,905 B2 | 2/2011 | John et al. |
| 7,919,831 B2 | 4/2011 | Motoki et al. |
| 7,966,073 B2 | 6/2011 | Pless et al. |
| 7,988,917 B2 | 8/2011 | Roesicke et al. |
| 8,116,875 B2 | 2/2012 | Osypka et al. |
| 8,121,694 B2 | 2/2012 | Molnar et al. |
| 8,195,174 B2 | 6/2012 | Lee et al. |
| 8,239,030 B1 | 8/2012 | Hagedorn et al. |
| 8,290,596 B2 | 10/2012 | Wei et al. |
| 8,301,265 B2 | 10/2012 | Starkebaum |
| 8,349,554 B2 | 1/2013 | Bahrami et al. |
| 8,380,316 B2 | 2/2013 | Hagedorn et al. |
| 8,419,716 B2 | 4/2013 | Weissenrieder-Norlin et al. |
| 8,473,063 B2 | 6/2013 | Gupta et al. |
| 8,494,627 B2 | 7/2013 | Bikson et al. |
| 8,554,324 B2 | 10/2013 | Brocke |
| 8,583,237 B2 | 11/2013 | Bedenbaugh |
| 8,591,392 B2 | 11/2013 | Bentwich et al. |
| 8,626,259 B2 | 1/2014 | Besio |
| 8,706,181 B2 | 4/2014 | Stypulkowski et al. |
| 8,795,174 B2 | 8/2014 | Manicka et al. |
| 8,818,515 B2 | 8/2014 | Bikson et al. |
| 8,838,247 B2 | 9/2014 | Hagedorn et al. |
| 8,874,220 B2 | 10/2014 | Draghici et al. |
| 8,874,227 B2 | 10/2014 | Simon et al. |
| 8,880,173 B2 | 11/2014 | Diubaldi et al. |
| 8,903,494 B2 | 12/2014 | Goldwasser et al. |
| 8,938,301 B2 | 1/2015 | Hagedorn |
| 8,979,837 B2 | 3/2015 | De La Rama et al. |
| 8,989,863 B2 | 3/2015 | Osorio |
| 9,002,458 B2 | 4/2015 | Pal et al. |
| 9,080,918 B2 | 7/2015 | Fishel et al. |
| 9,186,505 B2 | 11/2015 | Katsnelson |
| 9,393,430 B2 | 7/2016 | Demers et al. |
| 9,399,126 B2 | 7/2016 | Pal et al. |
| 9,433,774 B2 | 9/2016 | Dar et al. |
| 9,440,063 B2 | 9/2016 | Ho et al. |
| 9,440,070 B2 | 9/2016 | Goldwasser et al. |
| 9,486,618 B2 | 11/2016 | Wingeier et al. |
| 9,517,345 B2 | 12/2016 | Meffin et al. |
| 9,630,005 B2 | 4/2017 | Wingeier et al. |
| 9,643,001 B2 | 5/2017 | Wu et al. |
| 9,713,712 B2 | 7/2017 | Wingeier et al. |
| 9,731,127 B2 | 8/2017 | Kealey et al. |
| 9,757,561 B2 | 9/2017 | Wingeier et al. |
| 9,770,204 B2 | 9/2017 | Wu et al. |
| 9,782,585 B2 | 10/2017 | Wingeier |
| 9,802,042 B2 | 10/2017 | Wingeier et al. |
| 9,889,290 B2 | 2/2018 | Wingeier et al. |
| 9,913,973 B2 | 3/2018 | Yanaki |
| 9,981,128 B2 | 5/2018 | Wingeier |
| 10,238,869 B2 | 3/2019 | Wingeier et al. |
| 10,238,870 B2 | 3/2019 | Pilly et al. |
| 10,434,301 B2 | 10/2019 | Wingeier et al. |
| 10,485,443 B2 | 11/2019 | Wolber et al. |
| 10,512,770 B2 | 12/2019 | Wingeier et al. |
| 10,525,255 B2 | 1/2020 | Wingeier et al. |
| 11,039,775 B2 | 6/2021 | Wolber et al. |
| 11,123,544 B2 | 9/2021 | Wingeier et al. |
| 2001/0020145 A1 | 9/2001 | Satterfield et al. |
| 2002/0169485 A1 | 11/2002 | Pless et al. |
| 2004/0019370 A1 | 1/2004 | Gliner et al. |
| 2005/0165460 A1 | 7/2005 | Erfan |
| 2006/0111754 A1 | 5/2006 | Ansarinia et al. |
| 2006/0212093 A1 | 9/2006 | Pless et al. |
| 2006/0229502 A1 | 10/2006 | Pollock et al. |
| 2006/0259094 A1 | 11/2006 | Grinshpoon et al. |
| 2007/0015984 A1 | 1/2007 | Yeo et al. |
| 2007/0023779 A1 | 2/2007 | Hirose et al. |
| 2007/0027498 A1 | 2/2007 | Maschino et al. |
| 2007/0038265 A1 | 2/2007 | Tcheng et al. |
| 2007/0093706 A1 | 4/2007 | Gevins et al. |
| 2007/0118070 A1 | 5/2007 | Cormier et al. |
| 2007/0213783 A1 | 9/2007 | Pless |
| 2007/0237678 A1 | 10/2007 | Roesicke et al. |
| 2007/0237797 A1 | 10/2007 | Peyman |
| 2007/0238945 A1 | 10/2007 | Delic et al. |
| 2007/0250145 A1 | 10/2007 | Kraus et al. |
| 2008/0004676 A1 | 1/2008 | Osypka et al. |
| 2008/0021520 A1 | 1/2008 | Dietrich |
| 2008/0027345 A1 | 1/2008 | Kumada et al. |
| 2008/0161884 A1 | 7/2008 | Chandler et al. |
| 2009/0069803 A1 | 3/2009 | Starkebaum |
| 2009/0099627 A1 | 4/2009 | Molnar et al. |
| 2009/0105785 A1 | 4/2009 | Wei et al. |
| 2009/0187159 A1 | 7/2009 | Greger et al. |
| 2010/0030129 A1 | 2/2010 | Nitzan et al. |
| 2010/0152731 A1 | 6/2010 | De La Rama et al. |
| 2010/0152810 A1 | 6/2010 | Minogue et al. |

(56) References Cited

U.S. PATENT DOCUMENTS

| | | |
|---|---|---|
| 2010/0213070 A1 | 8/2010 | Oki et al. |
| 2010/0268287 A1 | 10/2010 | Celnik |
| 2010/0330589 A1 | 12/2010 | Bahrami et al. |
| 2011/0040291 A1 | 2/2011 | Weissenrieder-Norlin et al. |
| 2011/0054288 A1 | 3/2011 | Besio |
| 2011/0112590 A1 | 5/2011 | Molnar et al. |
| 2011/0118806 A1 | 5/2011 | Pascual-Leone et al. |
| 2011/0276112 A1 | 11/2011 | Simon et al. |
| 2011/0288610 A1 | 11/2011 | Brocke |
| 2011/0319975 A1 | 12/2011 | Ho et al. |
| 2012/0007832 A1 | 1/2012 | Lee et al. |
| 2012/0065699 A1 | 3/2012 | Bedenbaugh |
| 2012/0071947 A1 | 3/2012 | Gupta et al. |
| 2012/0078323 A1 | 3/2012 | Osorio |
| 2012/0143020 A1 | 6/2012 | Bordoley et al. |
| 2012/0184894 A1 | 7/2012 | Imran et al. |
| 2012/0191157 A1 | 7/2012 | Stypulkowski et al. |
| 2012/0226127 A1 | 9/2012 | Asjes et al. |
| 2012/0265261 A1 | 10/2012 | Bikson et al. |
| 2012/0271377 A1 | 10/2012 | Hagedorn et al. |
| 2012/0289869 A1 | 11/2012 | Tyler |
| 2013/0085347 A1 | 4/2013 | Manicka et al. |
| 2013/0113059 A1 | 5/2013 | Song et al. |
| 2013/0184779 A1 | 7/2013 | Bikson et al. |
| 2013/0204315 A1 | 8/2013 | Wongsarnpigoon et al. |
| 2013/0261706 A1 | 10/2013 | Mirro et al. |
| 2013/0281759 A1 | 10/2013 | Hagedorn et al. |
| 2014/0035043 A1 | 2/2014 | Lee et al. |
| 2014/0069212 A1 | 3/2014 | Fishel et al. |
| 2014/0148872 A1 | 5/2014 | Goldwasser et al. |
| 2014/0172041 A1 | 6/2014 | Draghici et al. |
| 2014/0277324 A1 | 9/2014 | Diubaldi et al. |
| 2014/0316505 A1 | 10/2014 | Yanaki |
| 2014/0350431 A1 | 11/2014 | Hagedorn |
| 2015/0005841 A1 | 1/2015 | Pal et al. |
| 2015/0065838 A1 | 3/2015 | Wingeier et al. |
| 2015/0066104 A1 | 3/2015 | Wingeier et al. |
| 2015/0088224 A1 | 3/2015 | Goldwasser et al. |
| 2015/0112153 A1 | 4/2015 | Nahum |
| 2015/0238759 A1 | 8/2015 | Katsnelson |
| 2015/0238762 A1 | 8/2015 | Pal et al. |
| 2015/0258327 A1 | 9/2015 | Chao et al. |
| 2015/0328467 A1 | 11/2015 | Demers et al. |
| 2015/0335877 A1 | 11/2015 | Jeffery et al. |
| 2015/0352357 A1 | 12/2015 | Wei et al. |
| 2015/0352364 A1 | 12/2015 | Meffin et al. |
| 2015/0360027 A1 | 12/2015 | Bachinski et al. |
| 2015/0374971 A1 | 12/2015 | Dar et al. |
| 2015/0375007 A1 | 12/2015 | Takeuchi et al. |
| 2016/0017558 A1 | 1/2016 | French |
| 2016/0022981 A1 | 1/2016 | Wingeier et al. |
| 2016/0022989 A1 | 1/2016 | Pfeifer |
| 2016/0175589 A1 | 6/2016 | Wingeier |
| 2016/0184585 A1* | 6/2016 | Kealey ............... A61N 1/36114 607/45 |
| 2016/0256105 A1 | 9/2016 | Boyle et al. |
| 2016/0303362 A1 | 10/2016 | Wu et al. |
| 2016/0346530 A1 | 12/2016 | Jeffery et al. |
| 2016/0360990 A1 | 12/2016 | Altshuler et al. |
| 2016/0361532 A1 | 12/2016 | Wingeier et al. |
| 2016/0361541 A1 | 12/2016 | Wingeier et al. |
| 2016/0366507 A1 | 12/2016 | Hou et al. |
| 2017/0021158 A1 | 1/2017 | Wingeier et al. |
| 2017/0065816 A1 | 3/2017 | Wingeier et al. |
| 2017/0182285 A1 | 6/2017 | Tyler et al. |
| 2017/0224978 A1 | 8/2017 | Lee |
| 2017/0224990 A1 | 8/2017 | Goldwasser et al. |
| 2017/0224991 A1 | 8/2017 | Wingeier et al. |
| 2017/0360321 A1 | 12/2017 | Wolber et al. |
| 2017/0361096 A1 | 12/2017 | Wingeier |
| 2017/0368344 A1* | 12/2017 | Ironi ................. A61N 1/36021 |
| 2018/0021565 A1 | 1/2018 | Dar et al. |
| 2018/0256887 A1 | 9/2018 | Wingeier et al. |
| 2018/0256888 A1 | 9/2018 | Wingeier et al. |
| 2019/0111255 A1 | 4/2019 | Errico et al. |
| 2019/0175910 A1 | 6/2019 | Wingeier et al. |
| 2019/0374766 A1 | 12/2019 | Wingeier et al. |
| 2020/0046247 A1 | 2/2020 | Wolber et al. |
| 2021/0106825 A1 | 4/2021 | Wingeier et al. |

FOREIGN PATENT DOCUMENTS

| | | |
|---|---|---|
| CN | 102427762 A | 4/2012 |
| CN | 102596021 A | 7/2012 |
| CN | 103517732 A | 1/2014 |
| CN | 204017145 U | 12/2014 |
| CN | 204411500 U | 6/2015 |
| EP | 1767147 A1 | 3/2007 |
| EP | 2449961 A1 | 5/2012 |
| EP | 2740935 A1 | 6/2014 |
| GB | 2479092 B | 8/2013 |
| JP | H10234713 A | 9/1998 |
| JP | 3287788 B2 | 6/2002 |
| JP | 2010152731 A | 7/2010 |
| JP | 2012183302 A | 9/2012 |
| KR | 20150088224 A | 7/2015 |
| KR | 101685124 B1 | 12/2016 |
| KR | 20170021158 A | 2/2017 |
| KR | 20170028197 A | 3/2017 |
| KR | 20180021565 A | 3/2018 |
| WO | 2004060477 A1 | 7/2004 |
| WO | 2008048471 A2 | 4/2008 |
| WO | 2009134763 A1 | 11/2009 |
| WO | 2013004763 A1 | 1/2013 |
| WO | 2013113059 A1 | 8/2013 |
| WO | WO-2014141213 A1 | 9/2014 |
| WO | WO-2015031510 A1 | 3/2015 |
| WO | 2016016015 A1 | 2/2016 |

OTHER PUBLICATIONS

European Search Report for European Patent Application No. 18764684.9 dated Nov. 12, 2020, 2 pages.

Final office action for U.S. Appl. No. 15/916,170 dated Jul. 15, 2019, 11 pages.

International Preliminary Report on Patentability dated Sep. 10, 2019, received for PCT Application PCT/US2018/021625, 16 pages.

International Search Report and Written Opinion dated May 14, 2018, received for PCT Application PCT/US2018/021625, 18 pages.

Non-final office action for U.S. Appl. No. 15/916,170 dated May 14, 2018, 11 pages.

Non-final office action for U.S. Appl. No. 15/916,170 dated Nov. 1, 2018, 12 pages.

Non-final office action for U.S. Appl. No. 16/683,839 dated Mar. 10, 2021, 8 pages.

Non-final office action for U.S. Appl. No. 17/410,868 dated Jun. 8, 2023, 18 pages.

* cited by examiner

Outer fabric

SYSTEM FOR ELECTRICAL STIMULATION

CROSS-REFERENCE TO RELATED APPLICATIONS

This application is a continuation of U.S. patent application Ser. No. 16/683,839, filed 14 Nov. 2019, which is a continuation of U.S. patent application Ser. No. 15/916,170 filed 8 Mar. 2018, which claims the benefit of U.S. Provisional Application No. 62/468,624 filed 8 Mar. 2017, U.S. Provisional Application No. 62/486,348 filed 17 Apr. 2017, U.S. Provisional Application No. 62/468,616 filed 8 Mar. 2017, and U.S. Provisional Application No. 62/526,643 filed 29 Jun. 2017, each of which is incorporated in its entirety by this reference. This application is related to U.S. application Ser. No. 14/470,683 filed 27 Aug. 2014, U.S. application Ser. No. 15/250,070 filed 29 Aug. 2016, U.S. application Ser. No. 14/470,747 filed 27 Aug. 2014, U.S. application Ser. No. 15/250,160 filed 29 Aug. 2016, U.S. application Ser. No. 15/295,008 filed 17 Oct. 2016, and U.S. application Ser. No. 15/657,915 filed 24 Jul. 2017, each of which is incorporated in its entirety by this reference.

TECHNICAL FIELD

This invention relates generally to the biosignals field, and more specifically to a new and useful electrode system for electrical stimulation.

BACKGROUND

Electrode systems in the biosignals field are used to transmit electrical signals to a subject and can be used to detect or measure biosignals from the subject. Current electrode systems for electrical stimulation and/or biosignal detection are, however, insufficient for many reasons including inadequate contact between the subject and the electrode(s) of a system, non-robust contact between the subject and the electrode(s) of a system, inadequate accommodation of individual anatomical variation across subjects, subject discomfort while using an electrode system, undesirable pivoting due to improper spatial configuration of electrodes or improper configuration of electrode contact forces with respect to the anatomy of the human head and/or individual anatomical variation, and/or limited use within multiple electrical simulation or biosignal detection paradigms.

Thus, there is a need in the biosignals field for a new and useful system for electrical stimulation. This invention provides such a new and useful system.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
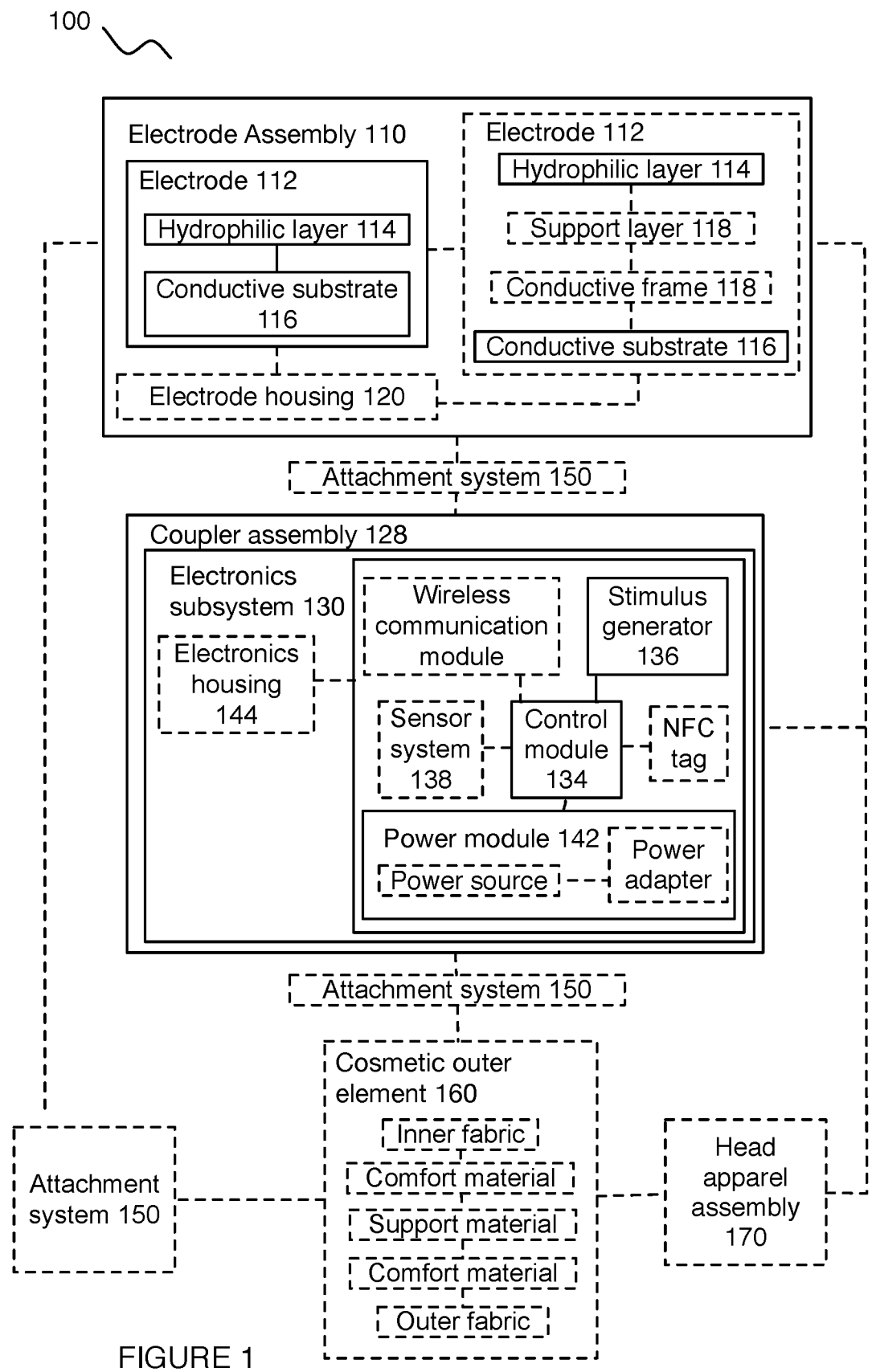
FIG. 1 depicts a schematic of a system for providing electrical stimulation and/or detecting biosignals of a user.
Figure 2A:
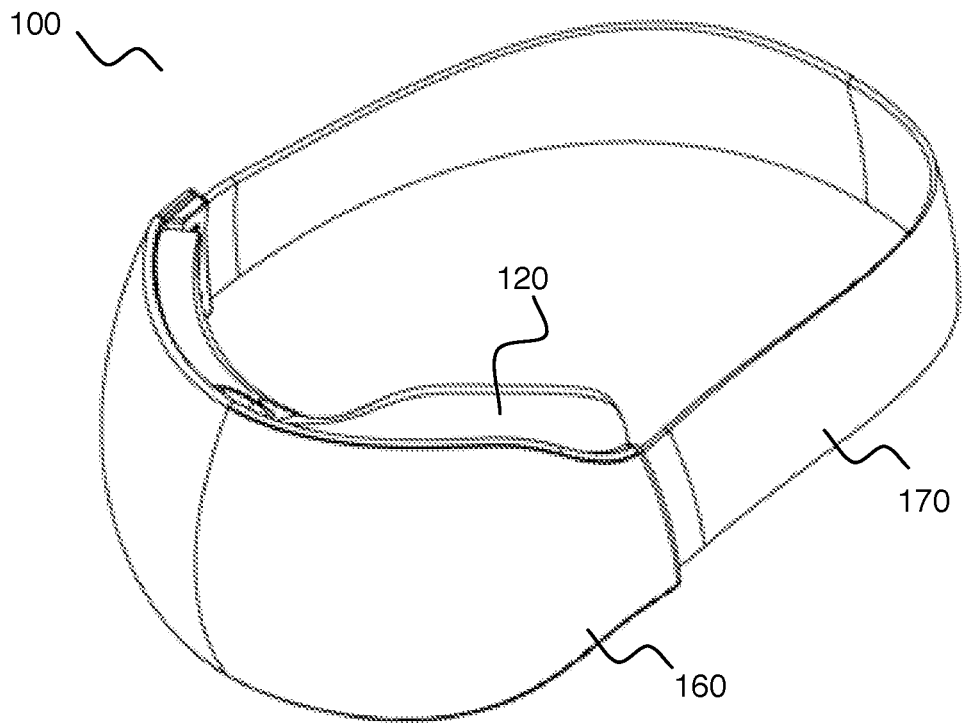
FIG. 2A depicts an assembled view of a variation of a system for providing electrical stimulation and/or detecting biosignals of a user.
Figure 2B:
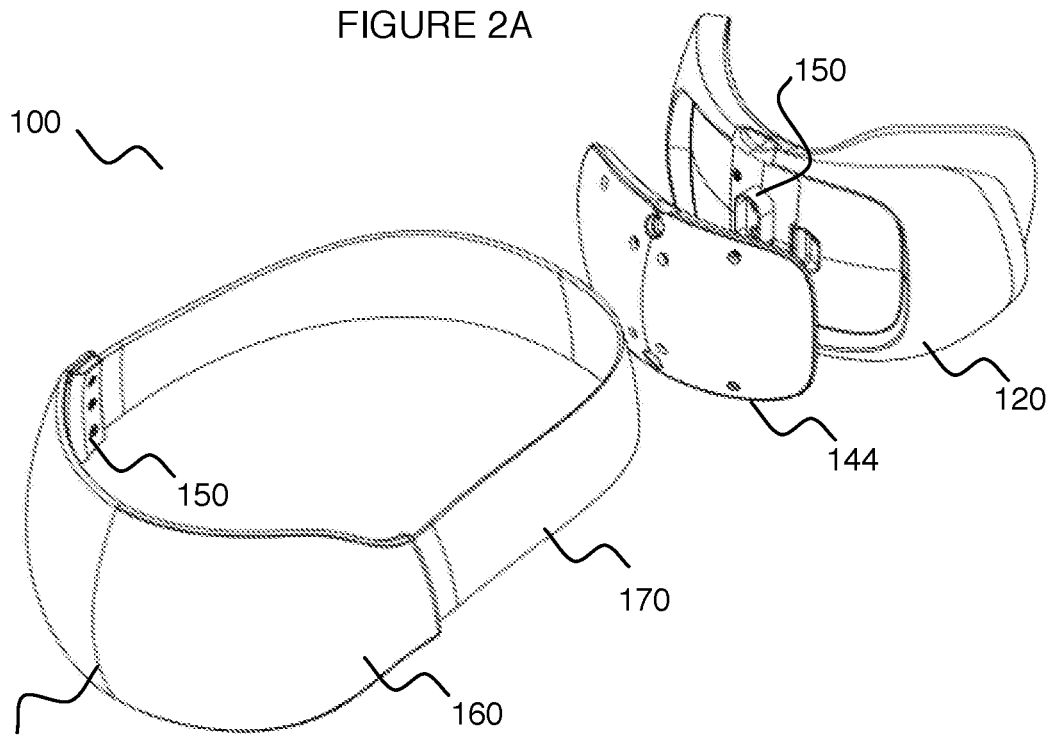
FIGS. 2B-2D depict exploded views of a variation of a system for providing electrical stimulation and/or detecting biosignals of a user.
Figure 2C:
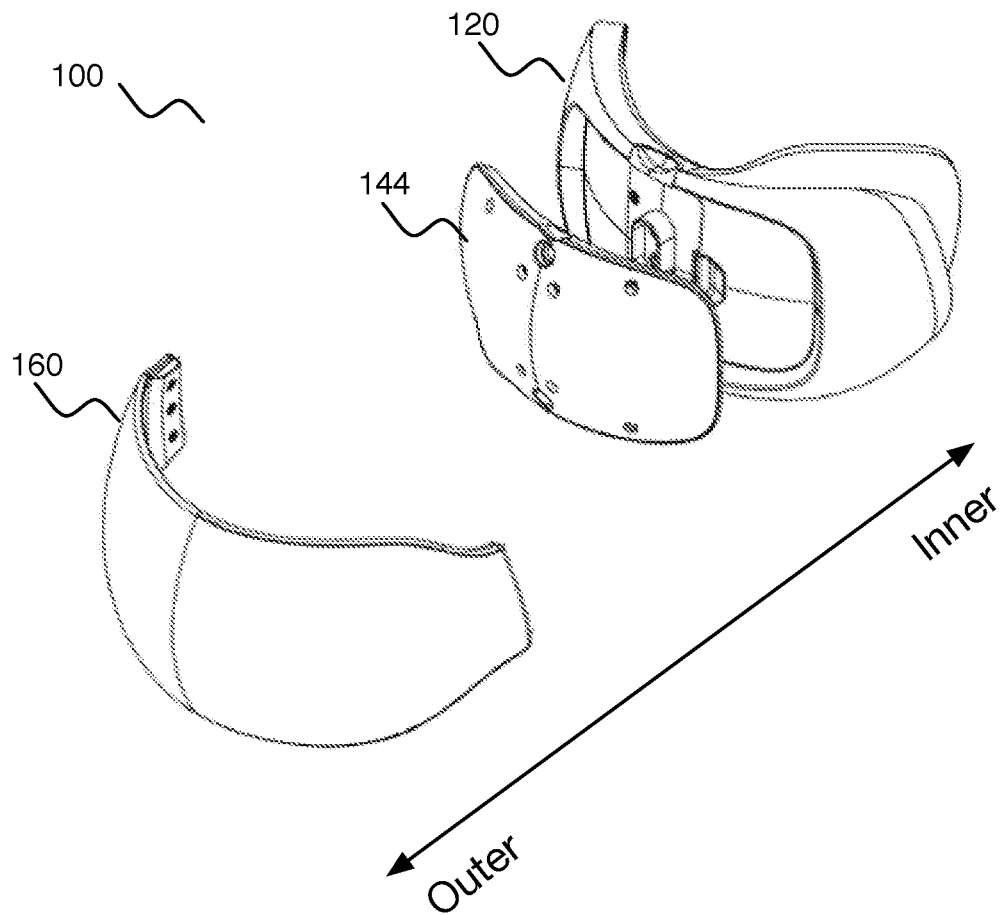
Figure 2D:
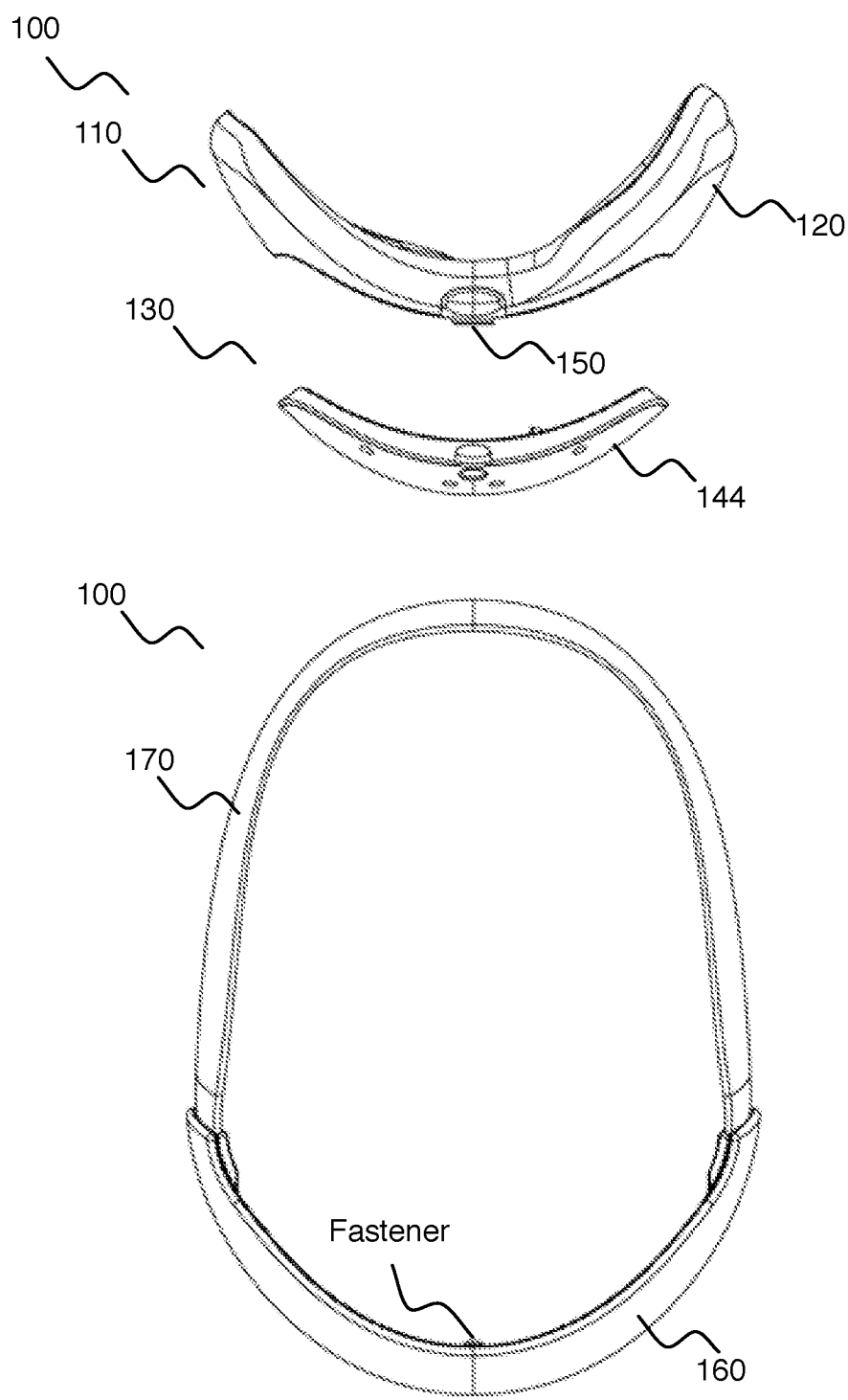
Figure 2E:
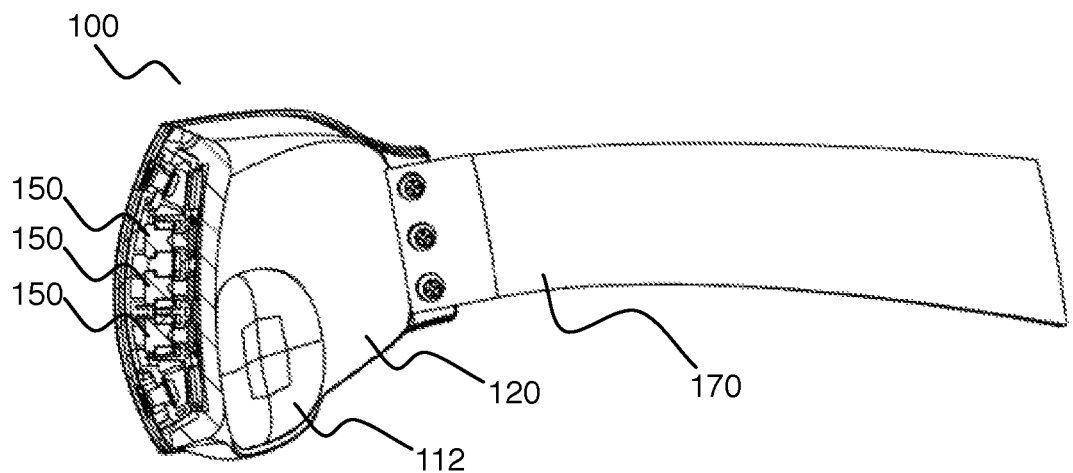
FIG. 2E depicts a cross-sectional view of a variation of a system for providing electrical stimulation and/or detecting biosignals of a user.

As shown in FIG. 1, an embodiment of the system 100 includes: an electrode assembly 110 including one or more electrodes 112 and a coupler assembly 128 electrically connected to the electrode assembly 110. In some variations (e.g., FIGS. 2A-2E), the system 100 can include an electrode housing 120, an electronics subsystem 130, an electronics housing 144, an attachment system 150, a cosmetic outer element 160, a head apparel assembly 170, and/or any other suitable component. The system 100 functions as an electrical stimulation device (e.g., to improve user performance, improve treatment of a user condition, improve user focus, improve user relaxation, improve user memory, improve user cognition, etc.), and can additionally or alternatively function to monitor/record biosignals (e.g., electroencephalography (EEG) signals) from a user, or have any other suitable functionality.

2. Benefits

There are numerous scenarios in which electrical stimulation applied (e.g., transcranially) to a user has been demonstrated to be beneficial. Electrical stimulation can be used for cognitive enhancement/training, such as to improve memory, focus, attention, problem solving, language abilities, mathematical abilities, etc. The use of electrical stimulation has also been shown to be beneficial for athletic performance, demonstrating improvements in the flexibility, speed, and/or skill of athletes. Electrical stimulation can also play a role in treating various medical conditions, such as neuropsychiatric conditions (e.g., depression, anxiety, Parkinson's disease, chronic pain, etc.), brain injuries (e.g., stroke), and others.

The wide variety of head shapes and sizes among the potential user base, however, has made it difficult to properly and precisely stimulate one or more predetermined brain regions among users with a single device. The inventors have discovered that designing the device with a flexible form factor can help properly and comfortably apply electrical stimulation to a wide variety of users. In some variations, this flexibility is at least partially obtained by one or more flexible and/or compliant housings. Additionally or alternatively, this flexibility can at least partially be achieved through flexible electrical interfaces, such as those constructed from one or more conductive polymers. Further additionally or alternatively, this flexibility can at least partially be achieved through compliant and/or adjustable electrodes (e.g., pivoting electrodes or electrodes lofted above a surface using material such as soft foam). This flexibility can also at least partially be obtained through a vertical alignment of an electronic attachment system, such that one or more electrodes can flex about a corresponding vertical axis (e.g., about an electrode rotational axis parallel the vertical alignment axis). These variations can provide the benefits not only of user comfort but also a proper location of electrical stimulation application.

3. System

As shown in FIG. 1, the system 100 includes: an electrode assembly 110 including one or more electrodes 112 and a coupler assembly electrically connected to the electrode assembly 110. In some variations (e.g., FIGS. 2A-2E), the system 100 can include an electrode housing 120, an electronics subsystem 130, an electronics housing 144, an attachment system 150, a cosmetic outer element 160, a head apparel assembly 170, and/or any other suitable component.

The system 100 functions to allow a user to receive electrical stimulation through a headpiece, wherein the electrical stimulation is preferably applied to predetermined regions of the scalp in order to target predetermined regions of the brain, but can additionally or alternatively be applied to regions chosen by the user, recommended by a clinician, chosen by an algorithm, randomly chosen, or otherwise determined. Additionally or alternatively, the system 100 can function to facilitate sensing (e.g., biometric sensing) of signals from a user in cooperation with, or in absence of, stimulation. The system 100 can additionally or alternatively incorporate or cooperate with one or more of: transducers (e.g., optical sensors, optical emitters, ultrasonic transducers, etc.), additional sensors (e.g., temperature sensors, activity detecting sensors, sensors associated with position, velocity, or acceleration detection, biometric sensors, etc.) for sensing signals from the user, additional sensors (e.g., temperature sensors, barometric pressure sensors, light sensors, microphones, etc.) for sensing signals from the environment of the user, and any other suitable module.

The system 100 can facilitate placement of a set of electrodes on a wide variety of user head morphologies (e.g., head shapes, head sizes, head contours, etc.), such as a variety of user forehead morphologies. This can be accomplished collectively through a variety of flexible materials used in the construction of the system 100 and their arrangement within the system 100. The system 100 can further facilitate maintenance of an electrode configuration that provides desired impedance characteristics and/or a desired type and location of contact at the user-electrode interface during placement and/or during use of the system 100. The system 100 can also include features configured to provide a high level of comfort in terms of wearability, as the user wears the system 100 during a period of stimulation treatment.

In some embodiments, the system 100 can be configured to interface with and/or include any of the embodiments, variations, and/or examples of electrode systems described in U.S. application Ser. No. 14/878,647 entitled "Electrode System for Electrical Stimulation" and filed on 8 Oct. 2015 and/or electrode systems described in U.S. application Ser. No. 14/470,683 entitled "Electrode System for Electrical Stimulation" and filed on 27 Aug. 2014, and/or electrode systems described in U.S. application Ser. No. 29/553,732 entitled "Biointerface Electrode" and filed on 4 Feb. 2016, which are each herein incorporated in its entirety by this reference; however, the system 100 can alternatively be configured to interface with and/or position any other suitable type of electrode or functional unit at the head of the user.

The system 100 is preferably configured to be worn by a user who is away from a research or clinical setting, such that the user can wear the system 100 while he or she is in a natural setting (e.g., at home, at a gym, outdoors, etc.). The system 100 can additionally or alternatively be configured to be operated by a user who is in a research setting, a clinical setting, or any other suitable setting. Furthermore, while some embodiments of the system are configured to be worn at the head of the user, alternative embodiments of the system 100 can be configured to be worn or coupled to any other suitable body region of the user.

In some embodiments, the system 100 can implement and/or facilitate implementation of one or more embodiments, variations, or examples of the method(s) described in U.S. application Ser. No. 14/470,747 entitled "Method and System for Providing Electrical Stimulation to a User" and filed on 27 Aug. 2014 and/or U.S. application Ser. No. 15/059,095 entitled "Method and System for Providing Electrical Stimulation to a User" and filed on 2 Mar. 2016, which are each incorporated in its entirety by this reference. However, the system can implement any suitable method of use.

As such, in embodiments and variations, the system 100 can be configured for application of one or more of: transcranial electrical stimulation (TES) in the form of transcranial direct current stimulation (tDCS), transcranial alternating current stimulation (tACS), transcranial magnetic stimulation (TMS), transcranial random noise stimulation (tRNS, e.g., band-limited random noise stimulation), transcranial variable frequency stimulation (tVFS), band-limited stimulation transformed to increase RMS power while minimizing transients and clipping, and any other suitable form of TES. Furthermore, in any of the above examples and variations, the system 100 can be configured to for delivery of stimulation as anodal stimulation and/or cathodal stimulation. In other examples, the electrical stimulation can additionally or alternatively comprise any other form of electrical stimulation (e.g., electrical muscle stimulation, etc.) configured to stimulate any other suitable region of the user's body, with any suitable penetration depth, and/or any suitable tissue structure (e.g., neural, musculoskeletal). In other examples, electrical stimulation to a body region such as the head may be delivered using a return path including a different body region such as the shoulder, and in such examples the electrode assembly 110 may include a connector such as a socket to which an electrode cable may be connected, or may itself include an electrode cable that may be extended to the different body region such as the shoulder.

In some variations, robust connection with the user provided by the elements (e.g., mechanical aspects) of the system 100 additionally or alternatively applies to transmission of non-electrical modes of stimulation according to other suitable methods. As such, the system 100 can additionally or alternatively be configured to transmit non-electrical modes of stimulation (e.g., ultrasound stimulation, optical stimulation) by using any appropriate transducer or set of transducers in place of or in addition to electrode contacts. For instance, one variation of the system 100 can be used to provide ultrasound transducing elements at a desired body region of the user, as facilitated by an array of protrusions configured to displace obstacles to ultrasound stimulation at the body region of the user. In this variation, ultrasound transducing elements can be configured at any suitable position along a length of a protrusion and/or at a distal end of a protrusion. Other variations can, however, be configured to incorporate any other element(s) for stimulating the user.

However, the system 100 can implement or facilitate implementation of any other suitable method(s).

3.1 System—Electrode Assembly

The electrode assembly 110, as shown in FIGS. 7A-7F, functions to provide electrical stimulation to a region of the user, such as the forehead region. Additionally or alternatively, the electrode assembly 110 can function to detect and/or measure and/or record one or more biosignals (e.g., EEG signals) from a user, provide comfort to a user, interface with a wide variety of user head morphologies, or perform any other suitable function.

The electrode assembly 110 is preferably held against the head (e.g., forehead, scalp, etc.) of a user through any or all of: compression, an adhesive, and/or a head assembly mechanism (e.g., strap, fastener, etc.), but can additionally or alternatively make contact with the head of a user through any other suitable mechanism. The electrode assembly can be contoured to the head of a user through any number of curved or shaped components, compliant components, flexible components (e.g., overall flexibility, flexibility about an inferior-superior axis, flexibility about a medial-lateral axis, etc.). In some variations, the electrode assembly 110 can include hollow portions (e.g., channels) for the retention and/or circulation of conductive solution (e.g., saline gel), to reduce the overall weight of the system 100, to contribute to the flexibility and/or compliance of the system 100, etc.

The electrode assembly 110 is preferably at least partially constructed from one or more compliant materials (e.g., foam, sponge, polymer, gel matrix, felt, etc.), which can function to hold and/or position one or more electrodes against a user. Additionally or alternatively, the electrode assembly can be constructed from one or more rigid materials (e.g., polymer, metal, etc.), which can function to add structural stability to the system 100. Further additionally or alternatively, the electrode assembly 110 can be at least partially constructed from any or all of: conductive materials, insulative materials, hydrophilic materials, hydrophobic materials, and/or any other materials.

The system 100 preferably includes a single electrode assembly 110 having multiple electrodes 112, but can additionally or alternatively include a single electrode assembly 110 having a single electrode 112, multiple electrode assemblies 110 (e.g., arranged on different regions of a user's head) each having one or more electrodes 112, or any number and combination of electrode assemblies 110. Multiple electrodes in the same electrode assembly 110 are preferably configurable electrically by the coupler assembly 128, but can alternatively be electrically connected in parallel, electrically connected in series, be connected to the same or different coupler assemblies 128, be connected to the same or different electronics subsystem(s) 130, or be otherwise electrically connected.

The system 100 can operate in one or more operation modes. In some variations, the system 100 can include an 'on' operation mode and an 'off' operation mode, wherein in the 'on' operation mode, one or more electrodes are actively applying an electrical stimulation (e.g., direct current) to a user and wherein in the 'off' operation mode, the one or more electrodes are not actively applying an electrical stimulation (e.g., alternating current) to the user. Additionally or alternatively, the system 100 can operate in any number of additional operation modes corresponding to any number of stimulation patterns (e.g., current definitions) applied by any number of electrodes. Further additionally or alternatively, the system 100 can operate in a receiving operation mode, wherein in the receiving operation mode, one or more electrodes are measuring and/or monitoring a parameter of an associated brain region, such as an EEG signal. The activation of and/or transition between operation modes can be triggered by any suitable stimulus (time of day, recurring, based on sensor data indicating placement of device, based on sensor data indicating readiness for or participation in training or learning, based on sensor data indicating physiological response to stimulation, based on vital signs or biosignals such as galvanic skin response or heart rate or heart rate variability (e.g., user is stressed), and/or selection by user (e.g., through user device, etc.)).

3.2 System—Electrode

The electrode assembly 110 includes a set of one or more electrodes 112 (e.g., as shown in FIGS. 7A-7F, 8, 9A-9C), which can each function and/or collectively function to apply electrical stimulation to one or more regions of the brain. Additionally or alternatively, an electrode 112 can function to detect and/or measure and/or monitor a parameter (e.g., biosignal) of brain activity.

Each of the electrodes 112 is arranged near or on the skin of a user, such as placed against a user's forehead, placed on a user's scalp (e.g., between head hairs, over head hair, etc.), placed partially over hair on a user's scalp, placed on a user's neck, placed near a user's spinal cord, or otherwise arranged near or on a user. However, one or more of the electrodes 112 can be arranged distal to the user's skin. The electrodes 112 can cooperatively or individually target (e.g., electrically stimulate) one or more particular brain regions, some or all of which can be described in an electrode naming convention and/or any other neural, anatomical, radiological naming convention, such as the 10-20 electrode system, 10-10 electrode system, 10-5 electrode system, the Brodmann naming convention (e.g., Brodmann areas), one or more bone-based (e.g., skull) naming conventions, and/or any other naming convention.

The system 100 preferably includes multiple electrodes (e.g., two electrodes, three electrodes, an array of electrodes, etc.), but can alternatively include a single electrode (e.g., single electrode targeted to a specified brain region, large electrode covering multiple brain regions, etc.). In one variation, a first electrode functions to target (e.g., is arranged proximal to) one or more frontal left hemispheric brain regions (e.g., F3 electrode region, left supraorbital (LSO) brain region, any electrode region, etc.) and a second electrode functions to target one or more frontal right hemispheric brain regions (e.g., F4 electrode region, right supraorbital (RSO) brain region, any other electrode region, etc.). Alternatively, the two electrodes can exclusively target left hemispheric brain regions (e.g., the F3 and LSO), right hemispheric brain regions (e.g., F4 and RSO regions), or any number and combination of regions on any region/lobe of the brain (e.g., cerebellum, frontal lobe, parietal lobe, temporal lobe, occipital lobe, etc.) or any other region (e.g., spinal cord) of the neural system or body. In some variations, the electrode assembly can include three or more electrodes (e.g., arranged proximal to the F3, F4, and RSO regions).

The set of one or more electrodes 112 is preferably arranged proximal to (e.g., overlaying, partially overlaying, next to/adjacent to, along a normal axis of, slightly displaced from, etc.) the targeted region of interest, but can additionally or alternatively be arranged with an offset from a region of interest, between multiple regions of interest, overlaying multiple regions of interest, or otherwise arranged.

For example, electrodes targeting one or more regions of the dorsolateral prefrontal cortex (DLPFC) (e.g., F3 and/or F4 regions) are preferably arranged superior to those targeting one or more supraorbital (e.g., LSO/RSO) regions, but can be otherwise arranged. The electrode assembly preferably includes equal numbers of electrodes on either side of the system (e.g., equal electrodes on the right and left sides of the system), but can alternatively include an uneven number of electrodes on either side of the system. The electrode assembly preferably includes a DLPFC electrode and a supraorbital electrode, but can alternatively include electrodes targeting any suitable region of the head.

In a first variation, the electrode assembly includes a first electrode (e.g., F3 electrode) arranged in a superior, left position (e.g., from a user's perspective), and a second electrode (e.g., RSO electrode) arranged in an inferior, right position.

In a second variation, the electrode assembly includes a first electrode (e.g., F3 electrode) arranged in a superior, left position (e.g., from a user's perspective), and a second electrode (e.g., LSO electrode) is arranged in an inferior, left position.

In a third variation, the electrode assembly includes a first electrode (e.g., F3 electrode) arranged in a superior, left position; a second electrode arranged in a superior, right position (e.g., F4 electrode); and a third electrode arranged in an inferior, right position.

In a fourth variation, the electrode assembly includes a single electrode, while the opposing side can include a cushion, strap, or other head retention mechanism that generates a compressive force against the user's head. In variations using a single electrode on the electrode assembly, a return path or reference electrode may be provided elsewhere on the body, e.g. placed on the head retention mechanism or by using a cable extending from the electrode assembly to the return path or reference electrode. However, the electrode assembly can include any suitable number of electrodes in any suitable arrangement.

Different electrodes can have different geometries and/or construction (e.g., number of layers, constituent materials, etc.), but can alternatively be substantially identical. The electrode construction can be determined based on: the targeted brain region, the location of the opposing electrode, or otherwise determined.

For example, in variants including opposing DLPFC and supraorbital electrodes, the DLPFC electrode (e.g., F3/F4 electrode) can have a larger stack up (e.g., a thicker hydrophilic layer 114, a thicker layer of intervening compliant foam (e.g., backing foam 118) between the conductive layer 116 and a support structure, more layers, lofted above a user forehead by a headpiece, etc.) than a supraorbital electrode (e.g., LSO/RSO electrode, which can lack compliant foam or include a thinner layer of compliant foam). This configuration can enable the system to conform to different head sizes and/or prevent system pivoting (e.g. pivoting of the system 100 around the axis defined by the line between the contact patches of two electrodes) due to the offset user contact points. The plane of the DLPFC electrode or portion thereof (e.g., conductive layer 116, hydrophilic layer 114, support structure 118, etc.) can be offset (e.g., elevated, lofted, etc.) from the plane of the supraorbital electrode or portion thereof by 0.1 mm, 1 mm, 5 mm, 10 mm, 20 mm, between 0.1 mm-10 mm, or by any suitable distance. However, the DLPFC electrode can be thinner than the supraorbital electrode (e.g., be closer to the user than the supraorbital electrode), be the same thickness (and/or have the same geometry, construction, and/or arrangement as) the supraorbital electrode, or be otherwise configured or arranged relative to the supraorbital electrode.

In some variations, two or more electrodes are arranged with a predetermined orientation and spacing with respect to each other, which can function to properly conform to a surface of the user (e.g., the forehead of a user) and/or a wide variety of users. In one variation, the angle between a tangent plane of a first electrode and a tangent plane of a second electrode can have a value of 13.5 degrees, a value between 5 and 20 degrees, a value between 8.5 and 18.5 degrees, a value between 10 and 15 degrees, or any other value or range of values. In a specific example, for instance, the angle between a first tangent plane and a second tangent plane, the first tangent plane tangent to a first center point of an inner broad surface of a first of the set of electrodes and the second tangent plane tangent to a second center point of an inner broad surface of a second of the set of electrodes, has a value between 8.5 and 18.5 degrees. In the variation shown in FIG. 9A-9C, any or all of a set of spacings/ dimensions (e.g., D1-D6) and/or any or all of a set of orientations/angles (e.g., A1-A8) can be used to locate one or more electrodes with respect to the other electrode(s). In a first example (e.g., in a relatively rigid electrode assembly 110), the dimensions D1-D6 have values of approximately or exactly 79 millimeters (mm), 41 mm, 40 mm, 30 mm, 17.5 mm, and 60 mm, respectively, and the angles A1-A8 have values of approximately or exactly 2.75 degrees (deg), 13.5 deg, 26.5 deg, 50 deg, 75 deg, 11.5 deg, 25.5 deg, and 20 deg, respectively. In a second example (e.g., in a moderately flexible electrode assembly 110), the dimensions D1-D6 can take on values of 79±15 mm, 41±15 mm, 40±10 mm, 30±10 mm, 17.5±10 mm, and 60±10 mm, respectively, and the angles A1-A8 have values of approximately or exactly 2.75±5 deg, 13.5±5 deg, 26.5±10 deg, 50±10 deg, 75±20 deg, 11.5±15 deg, 25.5±15 deg, and 20±15 deg, respectively. In a third example (e.g., in a flexible electrode assembly 110), the dimensions D1-D6 can take on values of 79±25 mm, 41±25 mm, 40±20 mm, 30±20 mm, 17.5±20 mm, and 60±20 mm, respectively, and the angles A1-A8 can take on values of 2.75±15 deg, 13.5±15 deg, 26.5±20 deg, 50±20 deg, 75±40 deg, 11.5±25 deg, 25.5±25 deg, and 20±25 deg, respectively. In a fourth example, the dimensions D1-D6 have values of approximately or exactly 84 mm, 40 mm, 40 mm, 35 mm, 14.5 mm, and 60 mm, respectively, and the angles A1-A8 have values of approximately or exactly 2.75 degrees, 13.5 degrees, 31 degrees, 50 degrees, 70 degrees, 11.5 degrees, 25.5 degrees, and 20 degrees, respectively. In a fifth example, the dimensions D1-D6 can take on values of 84±15 mm, 40±15 mm, 40±10 mm, 35±10 mm, 14.5±10 mm, and 60±10 mm, respectively, and the angles A1-A8 can take on values of 2.75±5 degrees, 13.5±5 degrees, 31±10 degrees, 50±10 degrees, 70±20 degrees, 11.5±15 degrees, 25.5±15 degrees, and 20±15 degrees, respectively. Additionally or alternatively, any of these dimensions and/or angles or any other set of dimensions and angles can take on any suitable range of values in order to conform to a head of a user.

Figure 3:
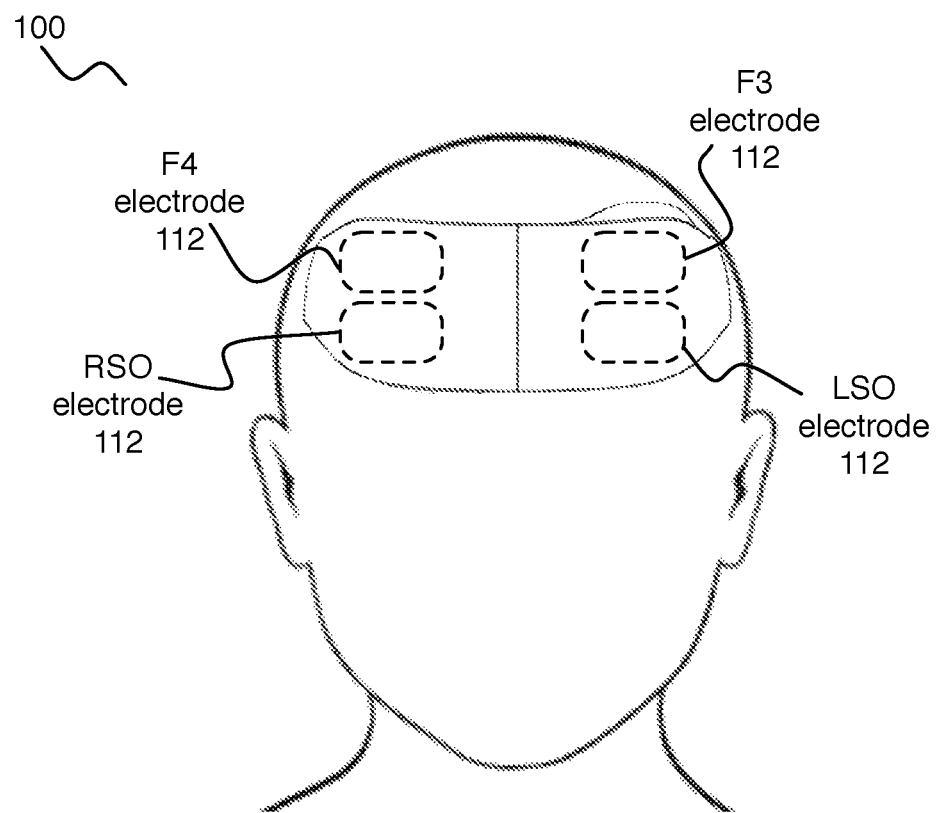
FIG. 3 depicts a variation of a set of electrode placement regions on a system for providing electrical stimulation and/or detecting biosignals of a user.
Figure 4A:
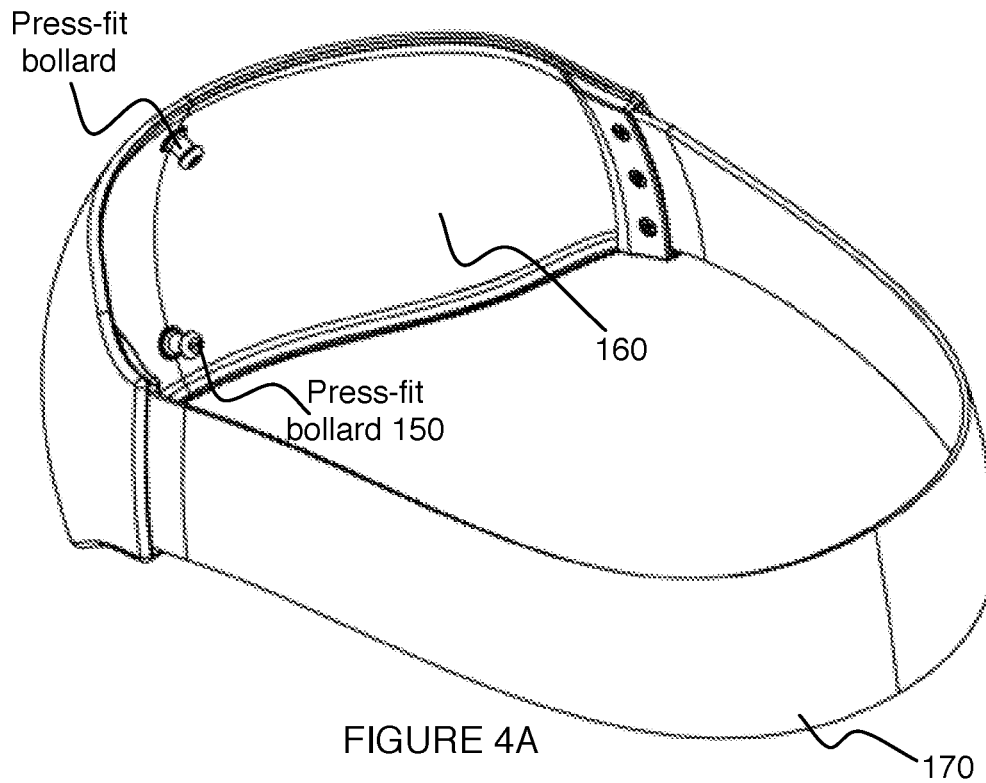
FIG. 4A depicts a variation of a cosmetic outer element attached to a head assembly mechanism.
Figure 4B:
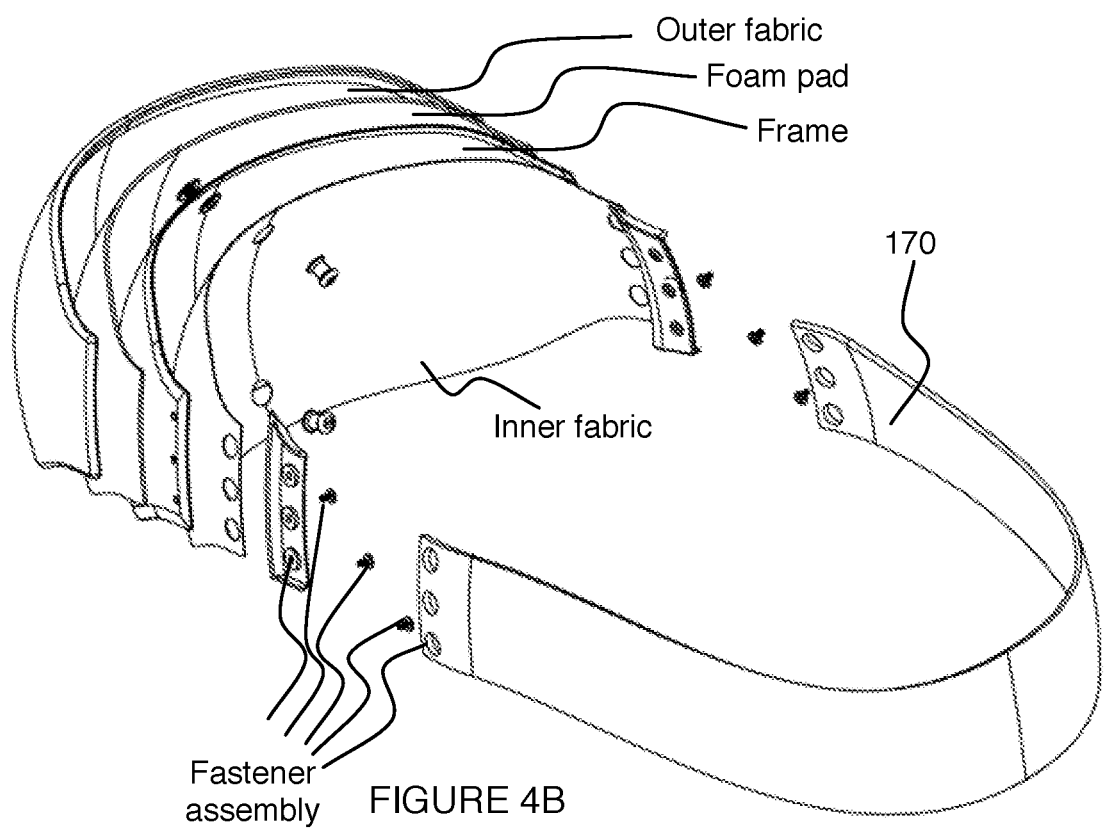
FIGS. 4B-4C depict exploded views of a variation of a cosmetic outer element attached to a head assembly mechanism.
Figure 4C:
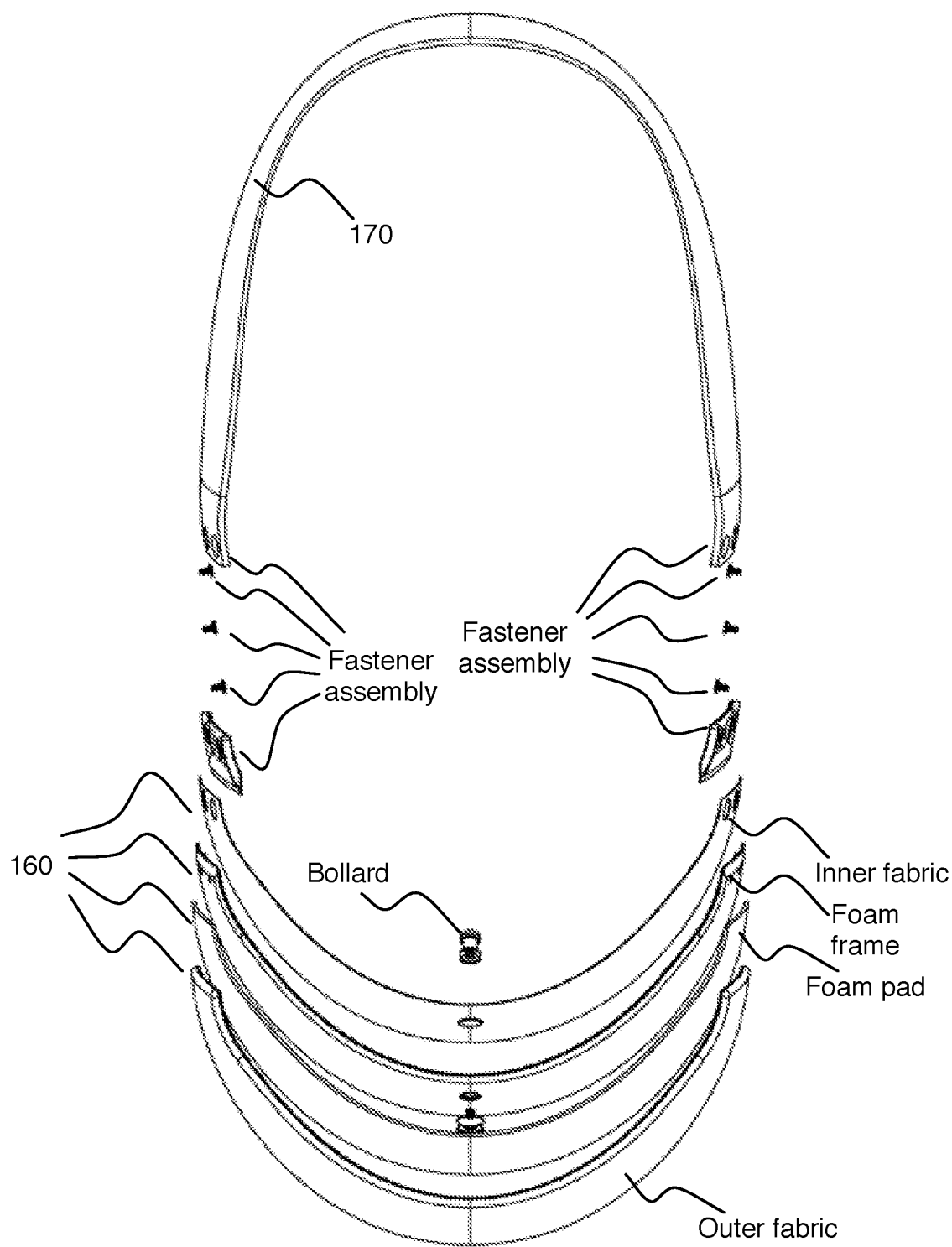
Figure 4D:
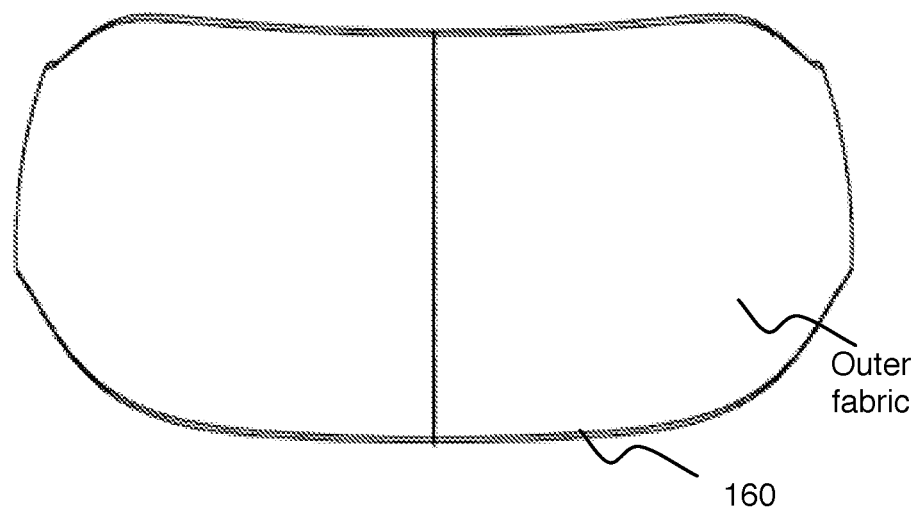
FIG. 4D depicts an outer broad surface of a variation of a cosmetic outer element.
Figure 4E:
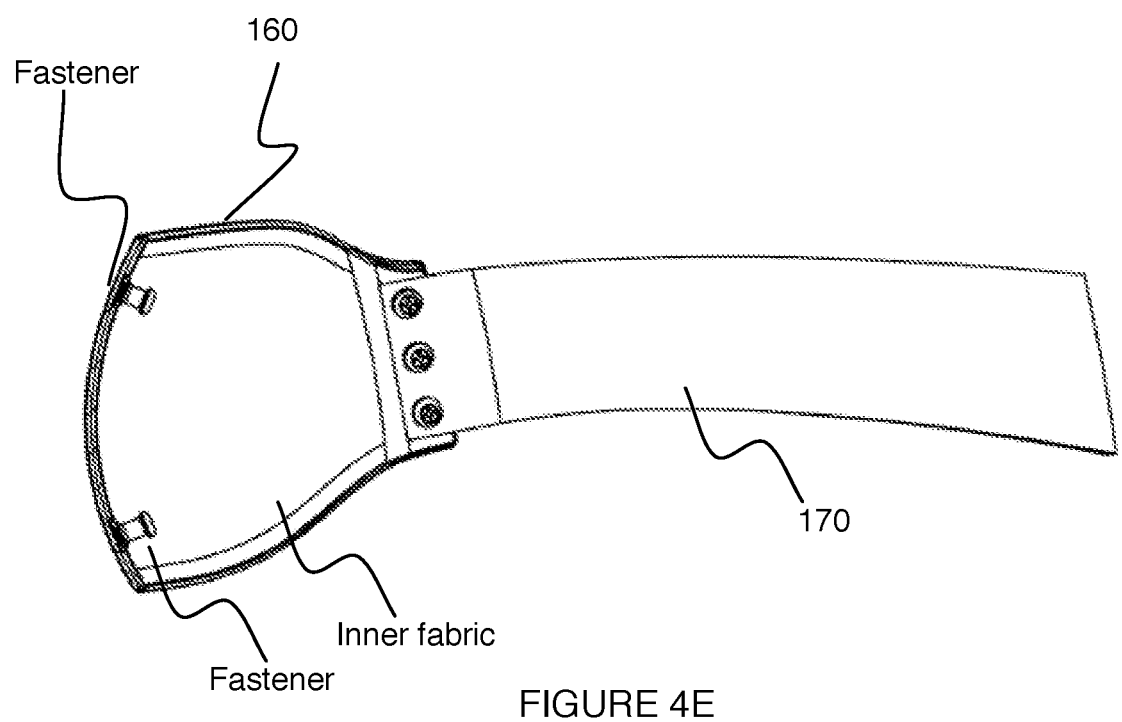
FIG. 4E depicts a cross-sectional view of a variation of a cosmetic outer element attached to a head assembly mechanism.

In one variation, as seen in FIG. 3, the electrode assembly 110 can include one or more electrodes arranged over any or all of: an F3 electrode region, an F4 electrode region, an LSO region, and an RSO region. In one example of this variation, the electrode assembly 100 can further include any number of electrodes arranged between any or all of the electrode regions (e.g., between the F4 and F3 electrodes), adjacent any or all of the electrode regions (e.g., adjacent an RSO electrode), and/or any number of electrodes arranged anywhere on the head of a user.

In a second variation, one or more electrodes can be arranged with a nonzero spacing with respect to one or more edges of a head assembly mechanism 170. In one example, for instance, an electrode can be electrically connected to a coupler assembly 128 (e.g., with a cable) and adhered to a user (e.g., with an adhesive) with a physical separation from the head assembly mechanism 170 (e.g., headband).

Each of the electrodes 112 is preferably constructed to have a curvature (e.g., a curvature of a broad surface, a set of curvatures of a broad surface, one or more curvatures of any other surface, etc.), which can function to conform to a region (e.g., forehead) of the user to provide comfort, facilitate proper placement, maintain proper placement, etc. Additionally or alternatively, one or more electrodes 112 can be constructed with a flat surface. In some variations, the electrodes 112 are constructed from a material compliant and/or thin enough to conform to a user without requiring one or more curved surfaces, or may be constructed to have a convex curvature and from a material that is compliant and/or thin enough that part or all of the convex curvature assumes a substantially concave shape and conforms to a region of the user when pressed against this region of the user.

Each of the electrodes 112 is preferably substantially rectangular (e.g., rectangular with rounded corners) in shape (e.g., outline/projection of a broad surface), but can additionally or alternatively be circular, ovoid, or have any other suitable shape. In a set of two or more electrodes 112, the electrodes 112 can have the same shape and size, different shapes (e.g., to cover/contour brain regions in different locations), and/or different sizes (e.g., to cover different sizes brain regions, different numbers of brain regions, etc.).

Figure 8:
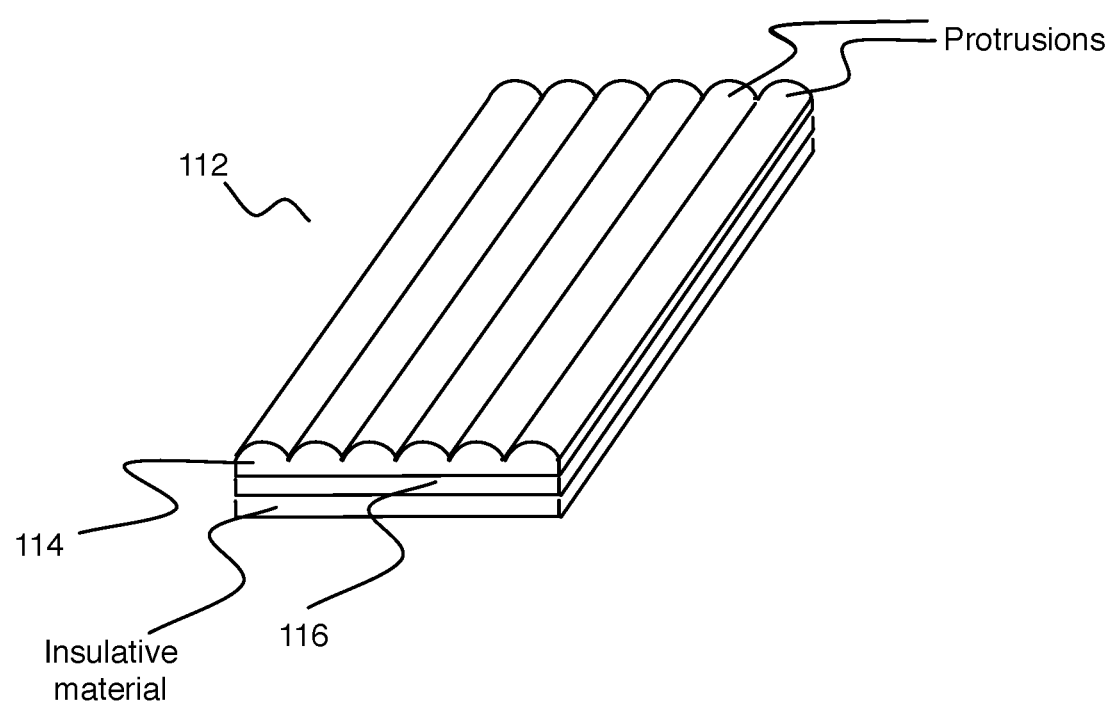
FIG. 8 depicts a variation of an electrode having a hydrophilic layer including a series of protrusions.
Figure 9A:
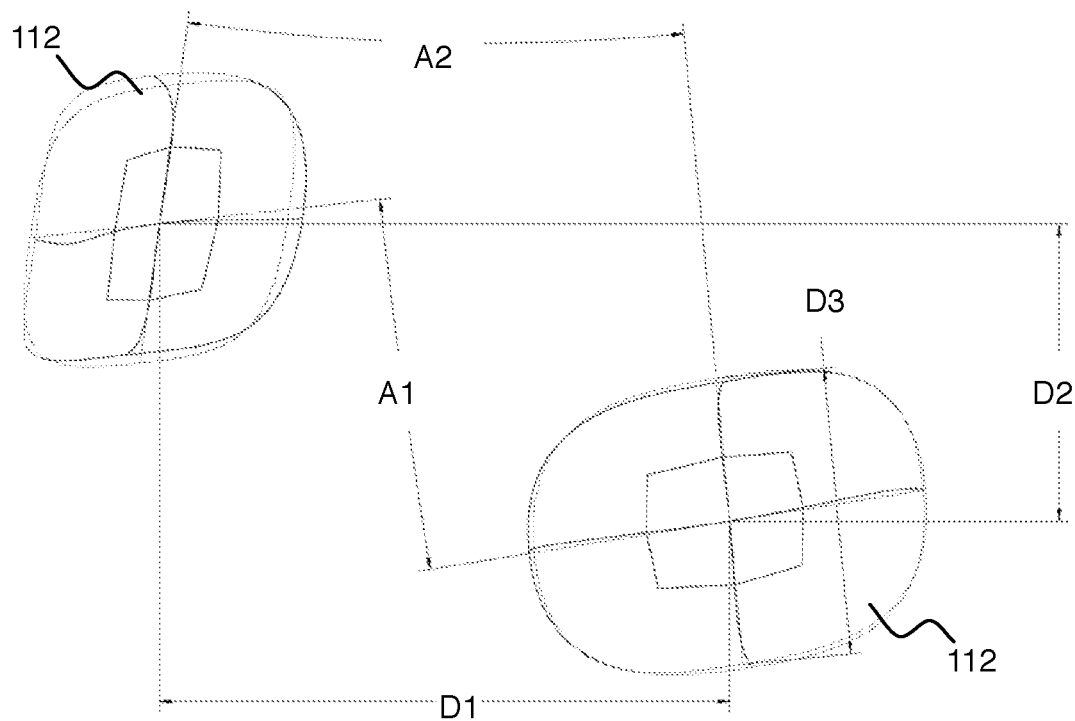
FIGS. 9A-9C depict a set of dimensions (D1-D6) and a set of angles (A1-A8) relating a set of electrodes in a variation of a system for providing electrical stimulation and/or detecting biosignals of a user.
Figure 9B:
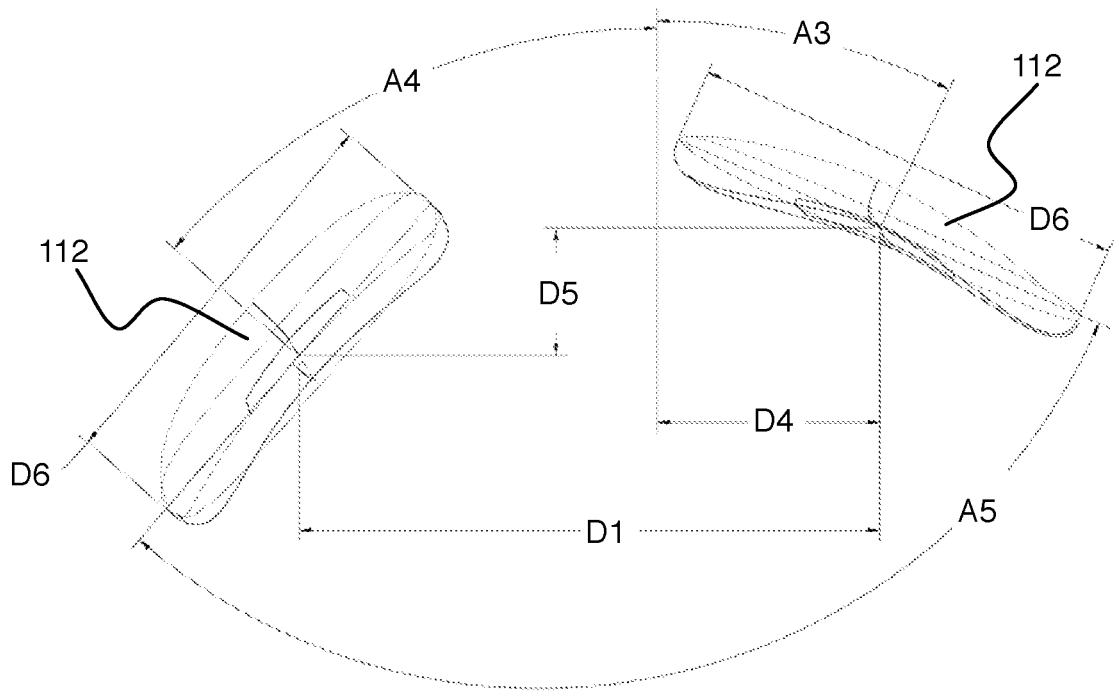
Figure 9C:
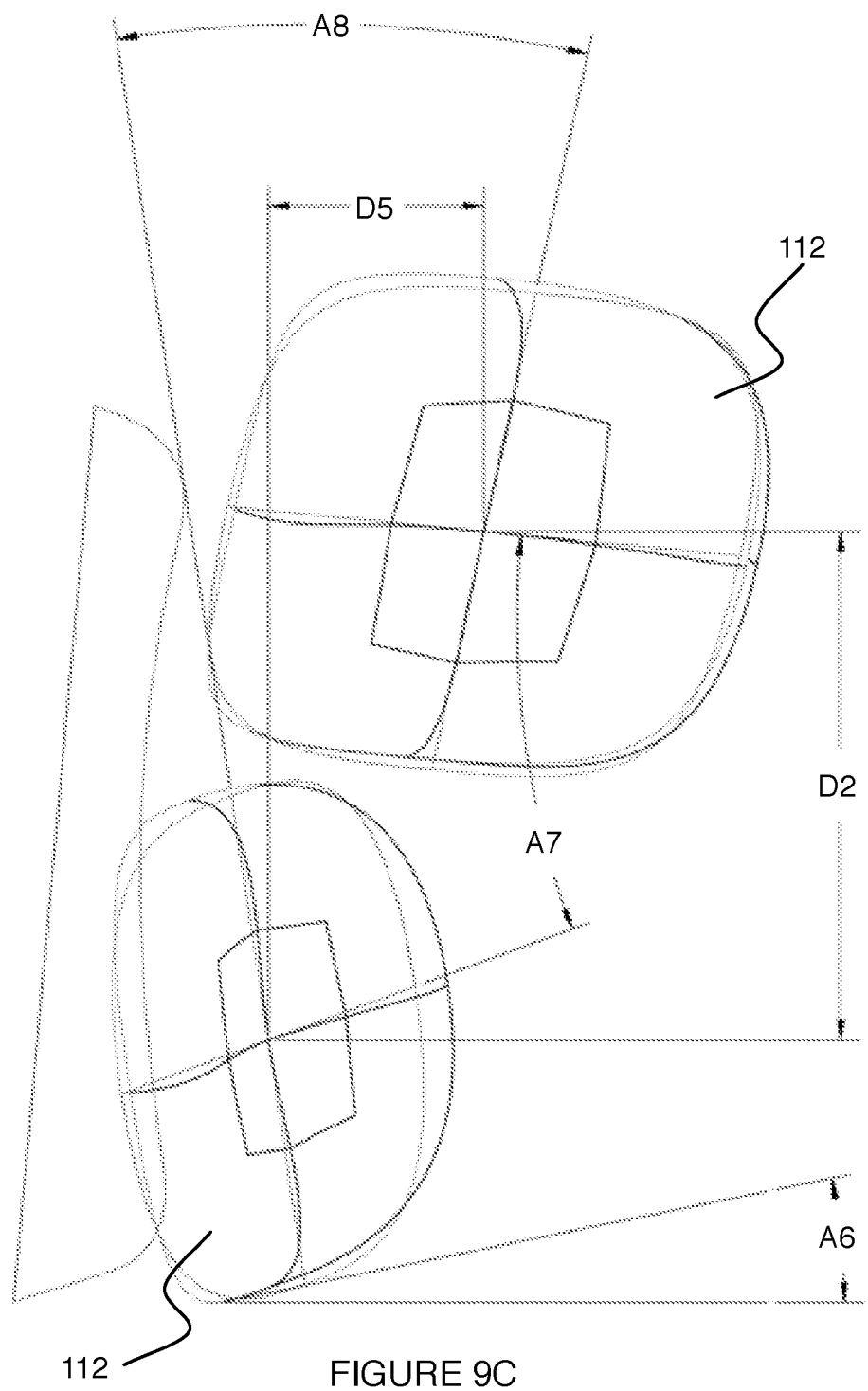

The surface of the electrode 112 arranged closest (e.g., most proximal) to the user (e.g., an inner broad surface; active surface; user interface) can be smooth (e.g., for enhanced comfort of the user), textured (e.g., to enhance retention of a conductive solution), include one or more protrusions (e.g., array or series of ridges, spherical bodies, pyramidal bodies, tubular bodies, etc. to comb through hair or otherwise improve electrode-user contact) as shown in FIG. 8, or have any other surface. The protrusions (e.g., bumps, merlons, ridges, nibs, comb teeth, pyramidal extensions, etc.) can be immediately adjacent (e.g., contiguous), be separated by spaces (e.g., crenels), or be otherwise configured. The protrusions are preferably compliant, but can alternatively be rigid or have any suitable stiffness. The surfaces of the protrusions proximal to the user (e.g., inner surfaces) can be flat, curved (e.g., convex, with a 1 mm radius or any suitable radius; concave, etc.), pointed, or otherwise configured. The protrusions are preferably arranged in a regular pattern or array on the electrode (e.g., wherein linear protrusions are arranged in parallel), but can alternatively be arranged in a matrix or in any suitable pattern. In one example, the protrusions are arranged with the ridges parallel to the vertical axis of the headpiece (e.g., an inferior-superior axis of the housing), with a projection parallel to the user's sagittal plane, or otherwise arranged. Additionally, any distal and edge surfaces of each electrode 112 can be smooth, textured, include one or more protrusions, or have any other surface.

Different electrodes 112 can have different inner broad surfaces, or have the same inner broad surfaces. In one example, the DLPFC electrodes can have protrusions, while the supraorbital electrodes can be flat. However, the DLPFC electrodes can be flat or otherwise configured, and the supraorbital electrodes can include protrusions or be otherwise configured.

Each of the electrodes and/or components thereof can be constructed from any or all of: a lamination procedure/process (e.g., foam and fabric lamination), a thermoforming process, one or more adhesive connections, one or more mechanical connections (e.g., retaining ring, grommets, sewing, etc.), a molding process (e.g., co-molding, injection molding, compression molding), an extrusion process, or any other method or process of manufacture.

Each of the electrodes 112 preferably includes two or more layers including a hydrophilic layer 114 (e.g., hydrophilic foam) and a conductive layer 116 (e.g., conductive polymer). Alternatively or additionally, one or more electrodes 112 can include a single layer (e.g., a conductive layer, a compliant conductive layer, a hydrophilic conductive layer, etc.), an insulative layer, a stiffening layer, and/or any other combination of layers.

3.3 System—Hydrophilic Layer

Each electrode 112 can include a hydrophilic layer 114, which can function to provide comfort to a user, retain a conductive solution (e.g., liquid electrolyte, conductive gel, conductive powder, saline solution, water, etc.), emit a conductive solution, conform to a variety of head morphologies, maintain electrode placement, or perform any other suitable function. The hydrophilic layer 114 is preferably the innermost layer (e.g., layer closest to the user, active layer, user interface layer, etc.) of the electrode 112 and defines an active face that is placed against the user (e.g., on the user's forehead), but can additionally or alternatively be arranged further away from the user with respect to another layer of the electrode 112 (e.g., behind another layer of the electrode 112, distal the user, etc.), form multiple layers of the electrode 112, or be arranged in any other way. The hydrophilic layer 114 may be constructed of a material that is fundamentally hydrophilic, such as cellulose or polyvinyl alcohol foam, or may be constructed of a material that is hydrophobic but is made hydrophilic by treatment such as with a surfactant.

The hydrophilic layer 114 is preferably constructed to have a curvature to conform to a user (e.g., be concave toward an active face, be convex toward the active face), but can alternatively be flat. The hydrophilic layer 114 can be rectangular (e.g., with rounded corners) in shape (e.g., shape of a broad surface of the hydrophilic layer 114, an outline or profile of the hydrophilic layer 114, etc.), circular, ovoid, or have any other shape. One or more surfaces can be smooth, textured (e.g., to retain a conductive solution), include one or more protrusions, or have any other surface type. In some variations (e.g., as shown in FIG. 8), the hydrophilic layer 114 is constructed with an array of surface protrusions (e.g., ridges, nibs, comb teeth, pyramidal extensions), which can function to enhance the distribution or retention of a conductive solution, reach the skin of a user (e.g., comb through hair), increase compliance/comfort of the electrode 112, or perform any other suitable function. In some variations, the hydrophilic layer 114 can have a thickness of exactly or approximately 4 mm uncompressed. In other variations, the hydrophilic layer 114 can have a thickness of exactly or approximately 2 mm uncompressed. In other variations, the hydrophilic layer 114 can have a thickness between 1 mm and 6 mm uncompressed, less than 10 mm uncompressed, or have any other thickness or range of thicknesses.

The hydrophilic layer 114 is preferably constructed from a porous material, but can alternatively be constructed from any suitable material. The porosity of the hydrophilic layer can include a range of pore sizes, have a substantially uniform pore size throughout, include a gradient of pore sizes (e.g., increasing from back to front, from right to left, or in any suitable direction along any suitable axis), or include any suitable distribution of pore sizes. The pore sizes can be between 10 micrometers-10,000 micrometers, 100-1,000 micrometers, or be any suitable pore size. The hydrophilic layer 114 is preferably constructed from a hydrophilic foam, such as a polyvinyl acetate (PVA) foam or sponge. Additionally or alternatively, the hydrophilic layer 114 can be constructed from a sponge, a hydrophobic foam, a cellulose foam, a shape memory foam, a comfort foam, polyolefin, cellulose, polyvinyl acetate sponge, a woven or sintered porous material, or a nonwoven felt material such as felted or extruded nylon fibers, cellulose fibers, a mixture of nylon and cellulose fibers, a closed-cell foam, an open-cell foam, a polymer (e.g., swellable polymer, swellable silicone, swellable gel, etc.), or any other suitable hydrophilic and/or compliant and/or porous material. In some variations, the hydrophilic layer 114 is further constructed from a conductive material, such as a conductive powder integrated within or on a surface of the foam. The hydrophilic layer 114 is preferably constructed from a relatively compliant material (e.g., elastic modulus less than 20 MPa, less than 50 MPa, less than 100 MPa, less than 1 GPa, between 20 and 100 MPa, etc.), but can additionally or alternatively be constructed from a relatively stiff material, or a material having any suitable properties.

The electrode 112 can include any number of hydrophilic layers 114. In some variations, the electrode includes a single hydrophilic layer 114 against the user's skin. In other variations, the electrode 112 can include one or more additional hydrophilic layers 114 (e.g., of higher stiffness than the first hydrophilic layer 114), which can function to better conform to the user, increase a thickness of the electrode 112, shield layers from a conductive fluid, retain a greater volume of conductive fluid, increase user comfort, or perform any other suitable function. Multiple hydrophilic layers 114 can be stacked along the electrode thickness, arrayed along the electrode height or width, or otherwise arranged.

The hydrophilic layer 114 preferably includes and/or provides an interface (e.g., conductive interface) between the electrode 112 and the user's skin. In some embodiments, this interface is provided in the form of a liquid electrolyte (e.g. 0.9% saline solution) carried by a hydrophilic layer 114. In some embodiments, the electrolyte is produced by the combination of water applied by the user (e.g. by splashing, spraying, or other means) mixing with salt (e.g. sodium chloride) pre-embedded (e.g. by drying of a brine solution in a porous hydrophilic layer 114), or otherwise created.

3.4 System—Conductive Substrate

Each electrode can include one or more electrically conductive substrates 116 (e.g., conductive backing). The conductive substrate 116 can function to establish an electrical connection between a hydrophilic layer 114 and another component of the system (e.g., stimulus generator, neurostimulation circuitry), for instance by forming a normal electronic connection to the neurostimulation circuitry and by forming an electrode-to-electrolyte interface with an electrolyte fluid contained within the hydrophilic layer. Additionally or alternatively, the conductive substrate 116 can function to establish an electrical connection between a hydrophilic layer 114 and another layer of the electrode 112, apply an electrical stimulation to a user, contribute structural support to an electrode 112, or perform any other suitable function.

The conductive substrate 116 is preferably arranged further away from the user (e.g., distally) than other layers of the electrode 112 but can additionally or alternatively be arranged closer to the user than other layers of the electrode, be the sole component of an electrode, be arranged along a perimeter of the electrode, or have any other suitable arrangement. The conductive substrate 116 is preferably positioned to form an electrode-to-electrolyte interface with electrolyte fluid or gel contained within the hydrophilic layer 114 and can additionally or alternatively be mechanically connected to the hydrophilic layer 114 (e.g., serve as a backing to the foam layer 114), electrically connected to the hydrophilic layer 114, and/or arranged in any other suitable way.

The conductive substrate 116 is preferably a similar shape as the hydrophilic layer 114, such that the conductive substrate 116 can be stacked/layered with the hydrophilic layer 114 and/or any other layers of the electrode 112, which can collectively function to conform to a head region (e.g., forehead) of the user. The conductive substrate 116 may include a proximal (e.g., toward the user) surface with geometric features such as ridges, bumps, or nibs that mate with inverse features present on the distal (e.g., away from the user) surface of the hydrophilic layer 114, to increase surface area of the interface between the conductive substrate 116 and hydrophilic layer 114 and/or minimize the path length between any point on the proximal (i.e., toward the user) surface of the hydrophilic layer 114 and the closest point on the conductive substrate 116. Additionally or alternatively, the conductive substrate 116 can be smaller than the hydrophilic layer 114 or have any other shape or size. The conductive substrate 116 is preferably between 0.1-1 mm thick, such as 0.8 mm thick, but can have any suitable thickness. In some variations, the conductive substrate 116 includes a frame (e.g., a support frame), wherein the frame can be arranged between the user and the conductive backing (e.g., as shown in FIG. 7C), which can function to electrically connect any or all of the conductive backing 116 to any or all of the electrode 112. Additionally or alternatively, the frame can be arranged to the side (e.g., medially, laterally, etc.) of the conductive backing, behind the conductive backing, along a perimeter of the electrode 112 or along/within any other region of the electrode 112. The conductive substrate 116 can additionally or alternatively include a frame extending in any other direction, a ring encircling the conductive substrate 116 and/or any other layer(s) of the electrode 112, or any other feature or component. In some variations, the conductive substrate 116 is simply a conductive component (e.g., metallic wire, clamp, bracket, etc.) attached to the hydrophilic layer (e.g., flexible foam) 114.

The conductive substrate 116 is constructed from an electrically conductive material. Preferably, the electrically conductive material is a conductive polymer, such as a conductive rubber (e.g., carbon rubber, conductive silicone rubber, nickel-graphite carbon rubber, graphite conductive rubber, silver copper silicone conductive rubber, etc.) or any other suitable conductive material. Additionally or alternatively, the conductive substrate 116 can include purely metallic materials (e.g., copper wire, gold plate, etc.), or any other conductive material(s) arranged in any suitable way.

In some variations, the conductive substrate 116 includes an electrical coupler, which functions to electrically and/or mechanically connect the conductive substrate 116 to another electrical component of the system 100, such as to a coupler assembly 128 (e.g., one or more elements of an electronics subsystem 130 within the coupler assembly 128) via an electrical attachment system 150 (e.g., conductive polymer body). The electrical coupler is preferably arranged along a second broad face of the electrode opposing the active surface of the electrode (e.g., arranged along the back of the electrode), but can alternatively be arranged along a side of the electrode, arranged along the active surface of the electrode (e.g., along the front of the electrode), or be otherwise arranged. The electrical coupler can be arranged along a portion of an electrode broad face, a protrusion extending from the electrode side, or have any suitable geometry. The electrical coupler is preferably flexible (e.g., with an elastic modulus less than 0.1 GPa), but can alternatively be stiff (e.g., with an elastic modulus of 50-90 GPa), or have any suitable stiffness.

In one example, the electrical coupler is a portion of the conductive substrate 116, such a conductive polymer extension (e.g., an extruded or molded conductive polymer arm; an extension of the conductive polymer from a side edge of the electrode 112, along the conductive substrate plane; etc.) or simply a surface of the conductive substrate 116 (e.g., a portion of the conductive surface broad face, such as a portion tracing the conductive substrate perimeter, an inner portion, a medial portion; etc), which makes contact with another electrical component of the system 100. In another example, the electrical coupler is a frame (e.g., conductive polymer frame connecting two or more electrodes together, a metallic frame, etc.). In a third example, the electrical coupler is one or more conductive wires (e.g., copper wires) attached to one or more conductive substrates 116.

Preferably there is one conductive substrate 116 for each electrode 112 in the device, but there can additionally or alternatively be multiple conductive substrates 116 for a single electrode (e.g., distributed throughout a multi-layer electrode), a single conductive substrate 116 for multiple electrodes 112, or any number and arrangement of conductive substrates 116.

3.5 System—Support Structure

The electrode 112 can include one or more support structures 118 (e.g., support layers), which can function to add structural stability to the electrode 112, retain one or more components (e.g., layers) of the electrode 112, attach and/or detach an electrode 112 from the system 100, establish an electrical and/or mechanical connection between components of the electrode 112, conform to the head of a user (e.g., by increasing the thickness of the electrode 112) and/or attach to the head of a user, or perform any other suitable function.

The support structure 118 can be of a similar shape and/or size as one or more layers of the electrode 112 (e.g., the hydrophilic layer 114), and span all or a majority of the electrode. This can allow, for instance, the support layer 118 to be easily stacked/layered with (e.g., in a recess of an adjacent layer of the electrode 112), laminated between, adhered to, embedded, molded, or otherwise arranged with one or more other layers/components of the electrode 112. In one example, the support structure 118 can be arranged (e.g., laminated) between a layer of insulating material and a layer of conductive substrate 116. In a second example, the support structure can be embedded within the conductive substrate 116 or other layer. However, the support structure 118 can span a portion of the electrode, such as the electrical coupler area of the electrode, extend along the edges of the electrode, extend uniaxially (e.g., along the electrode longitudinal axis, lateral axis, etc.), or along any suitable portion of the electrode.

The support structure preferably includes a material layer (e.g., a continuous layer, a woven layer, etc.), but can additionally or alternatively, the support structure 118 can include a frame (e.g., conductive frame electrically connected to the conductive substrate, polymer frame arranged around the perimeter of the electrode 112, polymer frame arranged between layers of the electrode 112, etc.), a ring (e.g., retaining ring holding multiple layers of the electrode 112 together, snap ring, etc.), reinforcement plate (e.g., metallic plate, polymer plate, magnetic plate, etc.), set of posts (e.g., arranged within or between layers of the electrode 112; arranged in an array; arranged in a radiating pattern from a central or peripheral connection point to one or more edges of the electrode; linked or intersecting; cooperatively forming a truss; etc.), mesh layer or lining, or any other form factor in any arrangement.

The support structure(s) 118 is preferably pre-curved (e.g., with the radius of the electrode; with a radius smaller or larger than a scalp curvature at the target location), but can alternatively or additionally be flat, sinusoidal, or have any suitable geometry. In one variant, the support structure 118 is pre-curved with a radius smaller than the scalp curvature. In this variant, the support structure stiffness is preferably relatively low (e.g., between 20 GPa-60 Gpa), which can result in a large geometric change but a low applied force when conforming to the scalp. This can allow the elastic forces on the scalp to be approximately identical for a wide variety of curvatures.

The support structure 118 can be constructed from any suitable material, and in variations of the electrode 112 having multiple support structures 118, the support structures 118 can be constructed from the same or different materials. In some variations, the support structure 118 is relatively compliant, such as a foam or sponge, fabric (e.g., felt), inflatable element, polymer (e.g., rubber, silicone, resin, polyoxymethylene etc.), metallic springs (e.g., stamped, formed, printed, etc.), or other material. In a specific example, for instance, the support structure 118 can be a backing foam arranged behind (e.g., adjacent a broad surface away from the head of a user) a hydrophilic layer 114. The backing foam can be arranged in a recess of the hydrophilic layer 114, adhered to a surface (e.g., outer broad surface, inner surface, edge surface, etc.) of the hydrophilic layer 114, be held by compression of the device, or otherwise arranged. In other variations, the hydrophilic layer 114 is made of a relatively rigid material, such as a polymer (e.g., stiff plastic), metal, conductive polymer (e.g., conductive substrate), etc. In one example, for instance, the support structure 118 can include an electrode frame, wherein the electrode frame is arranged between a hydrophilic layer 114 and a conductive substrate 116. In a specific example, the electrode frame can function to establish an electrical connection between the hydrophilic layer 114 and the conductive substrate 116 but can additionally or alternatively function to establish a mechanical connection, provide mechanical support, or perform any other function. In another specific example, the support structure 118 can be an attachment piece, such as a ring (e.g., snap ring, retaining ring, clamp, etc.) configured to hold elements of the electrode 112 together or to connect the electrode 112 to other components of the system 100.

The electrode 112 can further include any number of insulative materials (e.g., as shown in FIG. 8), which can function to protect a user and/or any element of the system 100, facilitate a proper electrical connection between components elsewhere in the system 100, and/or perform any other suitable function. In one variant, the insulative material can electrically isolate the electronic conducting material from all or part of the environment, which can isolate electrochemical reactions to the active face of the conductive substrate 116 (e.g., the face contacting electrolyte in the hydrophilic layer 114). The insulative material can be arranged behind the conductive substrate 116, between the hydrophilic material and the support structure, or otherwise arranged. The insulative material preferably extends along the entire broad face of the electrode 112 in a layer, but can extend along only a portion of the electrode 112. In one example, the insulative material can be between 0.01-0.5 mm thick, such as 0.1 mm thick, but can have any suitable thickness. Alternatively, the electrode can lack insulative materials or layers. The insulative material is preferably electrically insulative, but can alternatively or additionally be fluidly insulative (e.g., fluid-impermeable, hydrophilic, etc.) or have any suitable fluid property.

3.6 System—Fasteners

The electrode 112, and/or any other component(s) of the system 100, can include any number, type, and arrangement of fasteners (e.g., fastener assemblies), wherein the fasteners function to hold one or more elements of the system 100 together. These can include any or all of: an adhesive, screw, nail, tie (e.g., nylon tie), gasket, press-fit connector (e.g., press-fit bollards), sewn element, ring (e.g., O-ring), seal (e.g., face seal, boss seal, dovetail seal, reciprocating seal, laminated seal, etc.), magnet, joint, hook-and-loop fastener, button, snap, strap, buckle (e.g., watch strap buckle), clamp, and/or any other suitable fastening component and/or means for fastening/attaching.

In one variation, the layers of the electrode 112 are laminated together.

In a second variation, the electrode 112 is attached to the system 100 using a face seal.

In a third variation, a set of magnets is used to retain the position(s) of one or more electrodes relative to an adjacent element of the system 100, such as a foam support.

3.7 System—Electrode Housing

The system 100 preferably includes an electrode housing 120 (e.g., as shown in FIGS. 7A-7E), which can function to support one or more electrodes 112, separate one or more electrodes 112 from each other, conform to the head of a user, serve as an attachment point for another component of the system, or perform any other function.

The electrode housing 120 (e.g., compliant base) can be connected to one or more electrodes 112, preferably at an inner broad surface (e.g., surface closest to the user, active surface, user interface, etc.) of the electrode housing, such that a broad surface (e.g., inner broad surface, active surface, user interface surface, etc.) of the electrode 112 is exposed and configured to be placed against the user.

The electrode housing 120 can include one or more retention mechanisms that function to mechanically retain the electrodes 112. The retention mechanism can optionally form a mechanically stable joint and fluidly seal the electrical connection from fluid ingress. The retention mechanisms preferably include recesses for the electrodes 112, wherein the electrodes 112 can be placed within the recesses. The recesses are preferably complimentary to the electrode profile, but can alternatively have any suitable shape. The electrodes 112 are preferably press-fit into the recesses, but can alternatively be retained by an interference fit, be retained by an electrode tongue fitting within a recess groove, or be otherwise mechanically retained. The recesses can optionally include compliance mechanisms arranged therein that facilitate electrode 112 deformation relative to the electrode housing 120. Examples of compliance mechanisms that can be used include: springs (e.g., biasing the electrodes away from the electrode housing 120, dampers, foam, or other deformation mechanisms capable of applying a restorative force against the retained electrode 112. Additionally or alternatively, the electrodes 112 can be attached using an adhesive, sewn into the electrode housing, co-molded with the electrode housing, attached through a lamination process, attached using a mechanical connection (e.g., press fit, gasket, interlocking strips, bollards, screws, etc.), attached by complimentary magnet arrays cooperatively generating an attractive force, or otherwise connected.

In some variations, an electrical coupler (e.g., conductive polymer frame) connected to one or more conductive substrates 116 can extend through the electrode housing 120. This can function, for instance, to establish an electrical connection between one or more conductive substrate(s) 116 and an electronic component of the system (e.g., controller, stimulus generator, etc.). In a specific example, for instance, two conductive substrates 116 can have electrical coupler extensions which converge in a common electrical coupler frame, wherein the electrical coupler frame extends through the electrode housing in a direction away from the user (e.g., along a normal axis of the user's forehead).

The electrical coupler(s) of one or more electrodes 112 preferably aligns with an electronic coupling assembly (e.g., conductive polymer body, attachment system 150 piece, etc.) of the electrode housing 120 when the electrode 112 is mounted to the electrode housing 120, but can alternatively be offset. In one variation, the electrode housing 120 includes a gasket, bead, raised strip, or other sealing mechanism encircling all or a portion of the electronic coupling assembly. In another variation, the electrode 112 includes a gasket, bead, raised strip, or other sealing mechanism encircling all or a portion of the electrical coupler. In yet another variation, both the electrode housing 120 and the electrode 112 include a gasket, bead, raised strip or other sealing mechanism. The sealing mechanism can be formed from the insulating layer, the support layer, secondary material, such as plastic or elastomer, or any suitable material. The opposing surface can optionally include a complimentary groove that seats the sealing mechanism. The sealing mechanism can function to form a fluid-impermeable seal (e.g., watertight seal, fluid-impermeable seal, etc.) against the opposing surface of the complimentary component (e.g., electrode housing 120 or electrode 112).

The electronic coupling assembly (e.g., attachment system 150) of the electrode housing can be integrated with the retention mechanism of the electrode housing, be adjacent to, paired with, proximal, concentric with, distant from, or be otherwise arranged relative to the retention mechanism.

The electrode housing 120 preferably includes one or more curved broad surfaces and/or curved edges, the curved surfaces/edges configured to conform to one or more parts of the user head, such as the forehead, scalp, ear, back of the head/neck, or any other part of the user. Alternatively, the electrode housing 120 can include only straight surfaces/edges (e.g., when the electrode housing 120 is constructed from a compliant material).

The electrode housing 120 is preferably constructed from a relatively flexible and/or compliant material (e.g., elastic modulus less than 3 GPa, less than 2 GPa, less than 1 GPa, less than 100 MPa, between 20 and 50 MPa, etc.), which can help the system 100 better conform to a variety of head shapes and sizes. The electrode housing 120 can be constructed from a foam or sponge, polymer (e.g., rubber, silicone, etc.), fabric (e.g., Nylon fabric, reinforced fabric, non-woven fabric, etc.), or any other material. Additionally or alternatively, the electrode housing 120 can be constructed (e.g., using 3D-printing or molding/casting based on user dimensions) from a rigid material (e.g., to add structural support, maintain electrode positions), such as a polymer (e.g., rubber, plastic, etc.), metal, or any other suitable material. Additionally or alternatively, the electrode housing 120 can have a nonuniform rigidity. For example, the portions of the electrode housing 120 behind the electrodes 112 can be flexible, while the remainder of the electrode housing 120 can be rigid. In a second example, the portions of the electrode housing 120 behind the electrodes 112 can be rigid, while the remainder of the electrode housing 120 can be flexible. However, the electrode housing 120 can be otherwise constructed.

The electrode housing 120 is preferably constructed from a hydrophobic material, which can function to repel a conductive solution (e.g., saline electrode gel), repel perspiration from a user, or perform any other function. Additionally or alternatively, the electrode housing can be only partially hydrophobic, or not hydrophobic at all. In some variations, the electrode housing 120 can function to hold the device in place on a user. An electrode housing 120 can, for example, consist of a frame which at least partially circumferentially wraps around the head of a user and holds a set of electrodes in place. In some variations, the electrode housing 120 is constructed from a combination of compliant and rigid materials (e.g. a plastic frame encased in foam).

The electrode housing 120 can include a single piece, a single piece for each electrode, multiple pieces for a single electrode, multiple layered pieces, or any number and arrangement of pieces. In some variations, the electrode housing 120 includes an inner piece connected to an outer piece, the electrodes mounted to the inner piece.

In a first variation, the electrode 112 includes a hydrophilic electrode foam 114 placed against the user, followed by, in a direction away from the user (e.g., along a normal axis of the user's forehead), a backing foam 118, electrode frame 118, snap ring 118, and conductive polymer (e.g., carbon rubber) backing 116, the conductive polymer backing 116 including a conductive polymer frame (e.g., further attached to a second electrode 112) which extends through foam electrode housing 120.

In a second variation, the electrode 112 includes a foam layer 114 attached to a conductive backing 116.

In a third variation, the electrode 112 includes a conductive backing 116 and a conductive solution (e.g., saline solution).

In a fourth variation, the electrode 112 includes a hydrophilic layer 114 layered over a conductive substrate 116 which is then layered over an insulative material.

3.8 System—Coupler Assembly

The system 100 can include a coupler assembly 128 (e.g., as shown in FIGS. 5A-5C and 6A-6B), which functions to connect the any or all of the electrode assembly 110 to a head apparel assembly 170. Additionally or alternatively, the coupler assembly 128 can function to connect any or all of the electrode assembly 110 to a cosmetic outer element 160, to apply an electrical stimulation to one or more electrodes 112, to protect one or more electronic components, and/or perform any other suitable function. In embodiments and variations, the coupler assembly 128 may be integrated with one or more electrode assemblies 110 and/or one or more head apparel assemblies 170; the coupler assembly 128 may also connect only to one or more electrode assemblies 110 and not to a head apparel assembly 170, for instance if the coupler assembly is designed to be held to the head by the user during use of the system 100.

The coupler assembly 128 includes an electronics subsystem 130, as shown in FIGS. 5A-5C and 6A-6B, which functions to apply an electrical stimulation to one or more electrodes 112. Additionally or alternatively, the electronics subsystem 130 can function to power the system 100 and/or connect the system 100 to an external power source, monitor neural activity of a user, receive input(s) (e.g., desired operation modes) from a user, send output(s) (e.g., notifications) to a user, or perform any other function.

The electronics subsystem 130 is preferably connected to the electrode assembly 110 and preferably arranged behind the electrode assembly 110 (e.g., further away from the user). Additionally or alternatively, the electronics subsystem 130 can be connected to any component of the system, make contact with the user, or be otherwise arranged. The device preferably includes one electronics subsystem 130, but can additionally or alternatively include multiple electronics subsystems, an electronic subsystem in communication with an external electronics subsystem (e.g., a user device such as a mobile phone), or any number of electronic subsystems 130.

The electronics subsystem 130 preferably includes an electronics base, such as a printed circuit board (PCB), a breadboard, or any other suitable base, wherein the electronics base functions to mechanically support and/or electrically connect components of the electronics subsystem 130. Additionally or alternatively, the electronics base can include a set of conductive wires, wherein the wires electrically connect components of the electronics subsystem 130. Components of the electronics module 130 can additionally or alternatively be mechanically supported by other elements of the system, such as an electronics housing or an electrode housing 120, or not mechanically supported in any specific arrangement. In one variation, the electronics subsystem 130 is mounted behind one or more of the electrodes 112 (e.g., distal from the user) within the electrode housing 120.

3.9 System—Control Module

The electronics subsystem 130 preferably includes a control module (e.g., controller, processor, etc.) 134, which functions to apply an electrical stimulus (e.g., through a stimulus generator) to a user through one or more electrodes 112. Additionally or alternatively, the control module 134 can function to store electrical stimulus patterns, share electrical stimulus patterns (e.g., between users through an application on a user device, the cloud, etc.), monitor device performance, implement a fail-safe (e.g., power shut-off in the event of overheating or stimulus parameter above a predetermined threshold, alarm, etc.), monitor and/or measure neural activity of a user, store and/or share neural activity recordings, or perform any other suitable function.

The control module 134 is preferably electrically connected to the electrode assembly 110, more preferably to one or more conductive backings 116, but can additionally or alternatively be in wireless communication with the electrode assembly 110 and/or any other element in the system 100. In one example, for instance, a stimulus generator/deliverer onboard the system 100 can be controlled (e.g., wirelessly) from a remote source, such as a processor in a user device or a remote server system. An onboard control module 134 is preferably connected (mechanically and/or electrically) to an electronics base (e.g., PCB) but can otherwise be arranged anywhere else in the system. In variations having an onboard control module 134, the onboard control module 134 can be wirelessly coupled to a control module 134 of an external device, such as a user device. Examples of the user device include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi transceiver(s), Bluetooth transceiver(s), cellular transceiver(s), etc.), or any other suitable component.

The control module 134 preferably includes one or more of: a controller (e.g., a microcontroller), processor (e.g., a microprocessor), system on a chip (SoC) or other integrated circuit, timing subsystem including a set of timers, and/or stimulus generator (e.g., multi-channel stimulus generator, set of stimulation control instructions, etc.), but can additionally or alternatively include any other circuitry, electronic component, or control unit configured to apply an electrical stimulus to a user.

The control module 134 can include data storage (e.g., to store stimulation patterns), which can be onboard the system 100 (e.g., in the form of a memory chip, memory card, etc.) or external to the system 100 (e.g., via wireless communication with a remote server, the cloud, etc.).

The control module 134 can also include a sensor system mounted to or integrated within any part of the system 100 (e.g., attached to the electrode housing 120, attached to the electronics housing 144, etc.). The system 100 can, for instance, include any one or more of: a moisture sensor, pressure sensor, contact sensor, optical sensor (e.g., light sensor, camera, etc.), orientation sensor (e.g., accelerometer, gyroscope, altimeter, etc.), audio sensor (e.g., microphone), or any other sensor. The sensor system can be used to implement fail-safes (e.g., activate alarm based on temperature sensor data and/or stimulus generator data), determine/trigger operational modes, or can be used for any other purpose.

In some variations, the control module 134 further includes one or more wireless communication components, such as an antenna, WiFi chip, Bluetooth chip, a near-field communication (NFC) system (e.g., NFC tag, NFC chip, etc., e.g. used for identification of an NFC-readable tag in the electrode assembly 110 for purposes such as confirming usage of the correct type of electrode assembly 110 or suggesting or requiring replacement of the electrode assembly 110 after a predetermined or algorithmically-determined level or type of usage), a radio-frequency identification (RFID) system (e.g., RFID tag, RFID chip, etc.), or any other component.

The control module 134 is preferably configured to implement one or more operation modes and/or apply one or more stimulation patterns to one or more electrodes 112, such as through one or more stimulus generators 136. The stimulation pattern preferably includes a current definition, wherein the current definition can include (or correspond to, be based on, etc.) any or all of a current amplitude (e.g., a static current amplitude (e.g., 1 milliampere (mA), 2 mA, less than 5 mA, etc.), a maximum current amplitude, a minimum current amplitude, etc.), a current waveform (e.g., sinusoidal, ramp, step, square, triangular, etc.), or any other form of current-related parameter. Additionally or alternatively, the stimulation pattern can include a voltage definition, power definition, heating command, or any other form of stimulus. The stimulation pattern can further include temporal parameters, such as, but not limited to: a duration of a stimulus pattern (e.g., 10 minutes of constant direct current stimulation, 20 minutes of on-off stimulation, etc.), a sequence of stimulation patterns (e.g., ramp-up followed by static hold), time of onset (e.g., apply a specified current definition at a specified time each day, upon detection of stimulation device placement on a user, etc.), a frequency of a current waveform, and/or a speed of propagation of a current definition. In some variations, the temporal parameters are determined using a timing subsystem including a set of timers. In some variations, a stimulation pattern or a set of stimulation patterns can be applied which dynamically propagate among and/or alternate between multiple electrodes. In one variation, each of a set of electrodes 112 can be independently controlled by the control module 134. This can be implemented through a separate control module 134 for each electrode, a single control module 134 having separate ports for electrode, or any other combination or configuration of single or multiple control modules 134.

The control module 134 can operate in operation modes, each of which preferably includes a current definition and a temporal parameter. Additionally or alternatively, the operation modes can include an on/off state, any form of stimulation pattern, only one of a current definition and a temporal parameter, or any other feature of electrode stimulation. Operation modes can be assigned and/or activated by a user (e.g., user makes selection through application on user device, sensor system of neurostimulation device detects a user voice command, user presses button on a control panel of the flexible backing, etc.), based on sensor data (e.g., pressure sensor detects when device has been placed on user), based on learned behavior of user (e.g., based on machine learning of user preferences and patterns), based on operation context (e.g., determined based on on-board sensor signals, remote device signals, etc.), or based on any other input. The operation modes of the control module 134 preferably at least include a first operation mode corresponding to a stimulated electrode (e.g., 1 mA direct current applied to electrode) and a second operation mode corresponding to an unstimulated electrode (e.g., no current applied to electrode). In one example of this, for instance, the first operation mode prescribes a current definition (e.g., pulsing direct current) and the second operation mode prescribes no current definition. The first operation mode of the control module 134 can further include any number of stimulation operation modes, wherein each of the stimulation operation modes prescribes a current definition and/or a temporal parameter. In one variation, for instance, there can be a set of operation modes each corresponding to different current values/amplitudes (e.g., 1 mA, 2 mA, 3 mA, etc.), different temporal parameters (e.g., current stimulation applied constantly for 20 minutes, current stimulation applied until turned off by a user, current stimulation pulsed for 1-ms durations spaced 1-ms apart, etc.). Additionally or alternatively, the control module can include any additional operation modes, a single operation mode, or any other operation mode.

3.10 System—Stimulus Generator

The electronics subsystem can include a stimulus generator (e.g., stimulus deliverer, current deliverer, current stimulus deliverer, etc.), which functions to transmit an electrical stimulus (e.g., based on an operation mode) to one or more electrodes 112 of the electrode assembly 110 and/or to operate in one or more operation modes. Additionally or alternatively, the stimulus generator can function to apply other stimuli, such as, but not limited to: a magnetic stimulus, ultraviolet (UV) light, heat, water, and/or any other stimuli. The stimulus generator is preferably electrically coupled to one or more electrodes (e.g., to the conductive layer(s) 116, the hydrophilic layer(s) 114, etc.), a control module 134, and a power module 142 of the system, but can additionally or alternatively be connected to a subset of these (e.g., when the control module 134 is remote), connected to any other element of the system, wirelessly connected to any element within or outside the system, and/or mechanically connected to any element. The stimulus generator is preferably electrically connected to the endpoints by a set of wires, but can alternatively be wirelessly connected to the endpoints or otherwise connected. The stimulus generator preferably comprises a current generator/current stimulus deliverer (e.g., that generates direct current, alternating current, both direct and alternating, etc.), but can additionally or alternatively include a voltage generator/voltage stimulus deliverer and/or any other suitable generator/stimulus deliverer configured to facilitate transmission of an electrical stimulus. As such, the stimulus generator can provide one or more current definitions, such as a direct current (DC), an alternating current (AC), an AC component superimposed on a DC component, a monophasic pulsatile waveform, a symmetrical biphasic pulsatile waveform, an asymmetrical biphasic pulsatile waveform, and any other suitable stimulation profile. The waveform produced by the stimulus generator preferably can be described by parameters comprising amplitude and duration, but additionally or alternatively comprising any other suitable parameter(s), such as modulation frequency, step size, mean amplitude, or root mean squared (RMS) value. Furthermore, any one or more of the above parameters can be configured to be modulated by the stimulus generator, such that the stimulus generator can produce any one or more of: modulated amplitudes, modulated frequencies, and modulated pulse durations (e.g., modulated parameters characterized by exponential decay, exponential growth, or any other suitable growth or decay profiles). While one stimulus generator is described, the electronics subsystem 130 can, in some variations, comprise more than one stimulus generator (e.g., a separate stimulus generator for each electrode), where the control module 134 is configured to multiplex output of the additional stimulus generators to one or more electrodes or subsections thereof.

3.11 System—Power Module

The system 100 can include a power module 142, which functions to enable the application of an electrical stimulus (e.g., current definition) to one or more electrodes of the system 100. Additionally or alternatively, the power module 142 can function to power a control module 134 and/or any other component of the system 100, provide an interface (e.g., adapter) for the system 100 to charge externally (e.g., through a USB port), or perform any other suitable function.

The power module 142 is preferably electrically connected to the control module 134 (e.g., a microprocessor), but can additionally or alternatively be electrically connected to the electrode assembly 110 (e.g., the conductive substrate 116 of an electrode 112), a stimulus generator, and/or any other electronic component of the system 100 or external to the system 100 (e.g., external power source). The power module 142 can also be mechanically connected to any component of the system 100, such as mounted to an electronics housing, an electrode assembly 110 (e.g., electrode housing 120), attached to a fastening means/head apparel assembly (e.g., elastic strap), attached with a cable in the form of a pocket unit, or arranged in any other suitable way.

The power module 142 can include a power source, such as a portable power source (e.g., battery, rechargeable battery, solar powered battery, etc.). Additionally or alternatively, the power module 142 can include one or more adapters to external power sources, such as a port or receptacle (e.g., USB port, USB-C port, USB-A port), a plug (e.g., for a wall outlet), a cable (e.g., USB cable, extendable USB cable), a connector/adapter configured for a vehicle power source (e.g., plug for a car cigarette lighter receptacle, connection to a vehicle USB port, etc.), and/or any other plug, adapter, or converter. Any or all of the adapters (e.g., ports, receptacles, plugs, etc.) can be located on an inner (e.g., closest to the user) broad surface of the electronics housing 144 but can additionally or alternatively be located on a surface (e.g., an outer surface) of the electrode housing 120, or anywhere else in the system 100.

In a first variation, the power module 142 includes a rechargeable battery and a USB port.

In a second variation, a power adapter (e.g., USB port) is arranged on the electronics housing 144 in such a way that prevents coupling of any or all of the electrode assembly 110 to an electronics housing 144, thereby preventing a user from applying electrical stimulation while the device is charging and/or connected to an external power source. In a specific example, a charging port is arranged proximal to an electrical attachment system 150 on the electronics housing 144, such that use of the charging port physically interferes from coupling the electrical attachment system on the electronics housing 144 to a corresponding electrical attachment system on the electrode housing 120.

In a third variation, the system 100 is configured for wireless charging. In a specific example, the electronics housing and/or any other component of the system 100 includes an inductive coil configured for inductive charging (e.g., on an inductive charging pad).

In a fourth variation, the power module 142 is a pocket unit configured to be placed in a pocket of the user. In an example, for instance, the power module 142 is a rechargeable battery pack attached to the system 100 with a cable such that the battery pack can be placed in the pocket of a user.

3.12 System—Electronics Housing

The coupler assembly 128 preferably includes an electronics housing 144 (e.g., FIGS. 5A-5C), which functions to contain one or more components of the electronics subsystem 130. Additionally or alternatively, the electronics housing 144 can function to contribute flexibility to the electronics subsystem 130, contribute structural support to the device, protect a user from the electronics subsystem 130, protect the electronics subsystem 130 (e.g., from a user, wear-and-tear, conductive solution, etc.), and or perform any other function.

The electronics housing 144 is preferably connected to an outer surface (e.g., broad surface furthest away from the user) of the electrode housing 120 but can additionally or alternatively be connected to an inner surface (e.g., broad surface closest to the user) of the electrode housing 120, partially or fully enclosed within the electrode housing 120 (e.g., between an outer piece and an inner piece of the electrode housing 120), directly connected to one or more electrodes (e.g., in the absence of an electrode housing 120), arranged at a distance from the device (e.g., as a pocket unit), or arranged in any other way with respect to any component of the device.

In some variations, the electronics housing 144 can be attached to the electrode housing 120 through a magnetic connection. In these variations, the electronics housing 144 can include one or more magnetic materials (e.g., ferromagnetic material, ferrimagnetic material, coin/disc magnet, metallic (e.g., aluminum, steel, etc.) plate, etc.) arranged in and/or on the electronics housing 144, which can reversibly couple to one or more corresponding magnetic materials (e.g., ferromagnetic material, ferrimagnetic material, coin/disc magnet, metallic (e.g., aluminum, steel, etc.) plate, etc.) in the electrode housing 120. In a specific example, the electronics housing 144 includes a set of disc magnets, which reversibly couple with a steel plate of the electrode housing 120.

The electronics housing 144 is preferably constructed with a similar profile (e.g., contours, curvature, etc.) as the head (e.g., forehead) of a user such that it can be layered with other elements of the device to conform to a head of the user. Additionally or alternatively, the electronics housing 144 can take on a number of morphologies and/or conform to various morphologies (e.g., shape memory material), have one or more flat surfaces, or have any other suitable geometry.

Figure 5A:
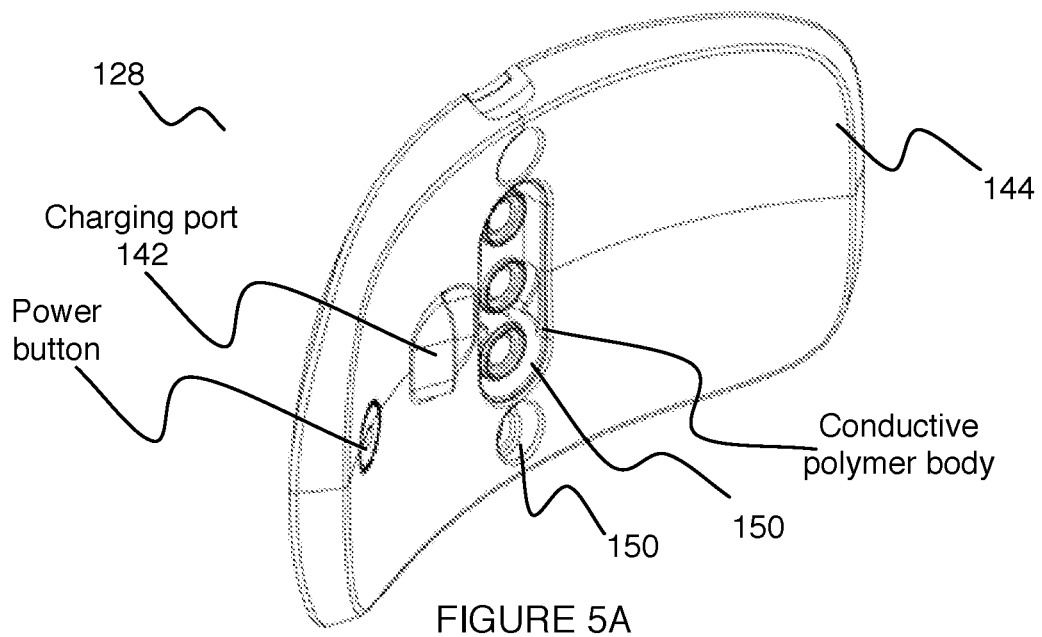
FIG. 5A depicts a view of a variation of a coupler assembly.
Figure 5B:
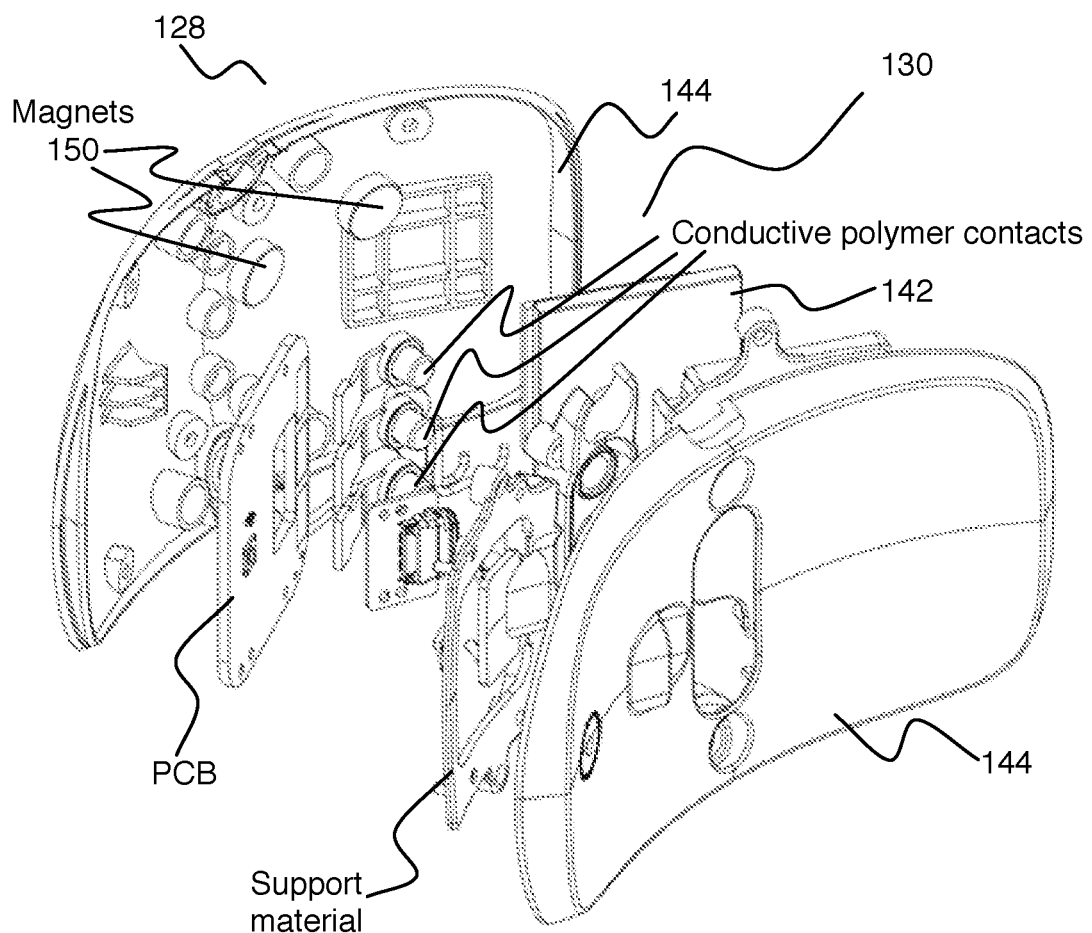
FIGS. 5B-5C depict exploded views of a variation of a coupler assembly.
Figure 5C:
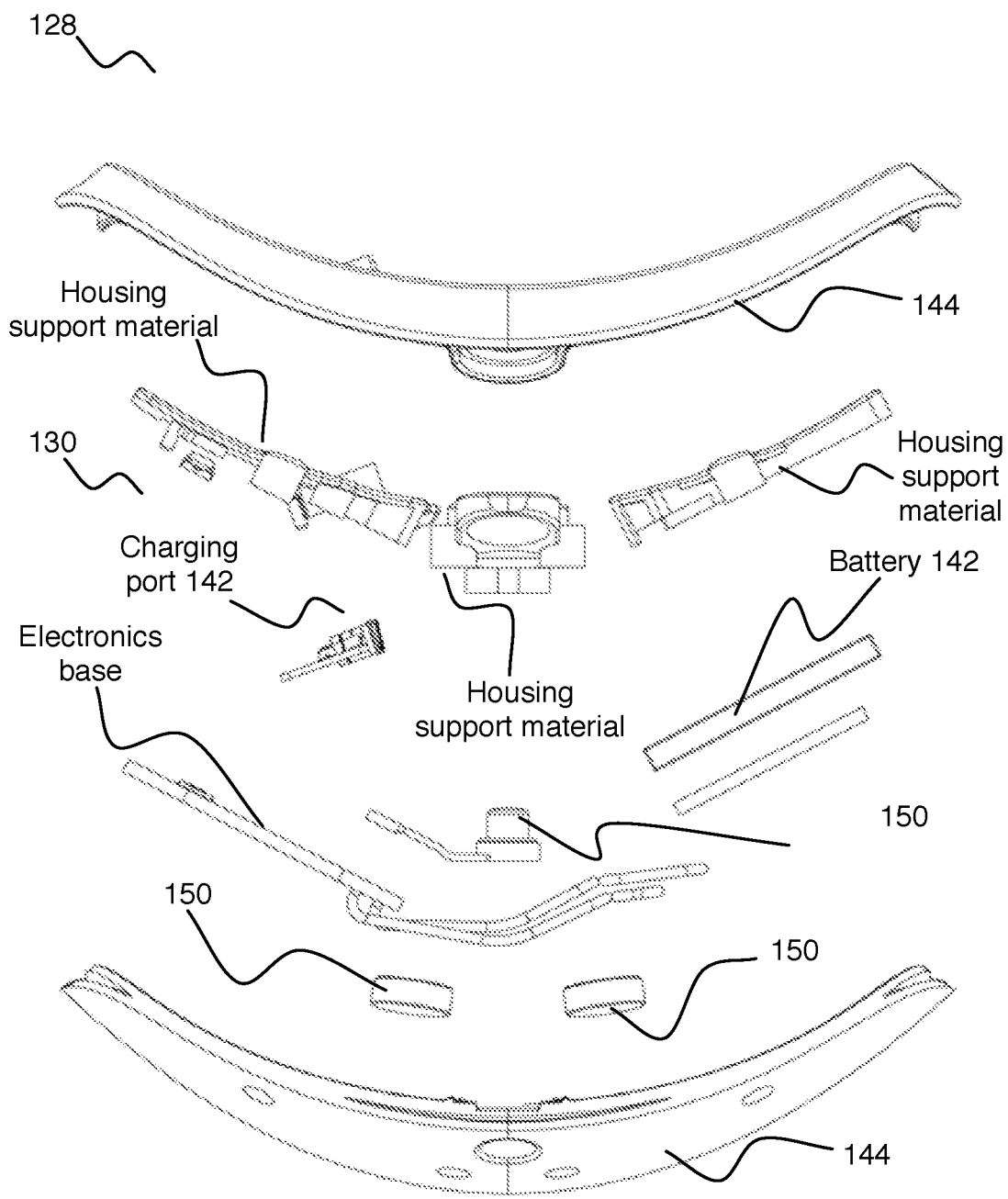

The electronics housing 144 is preferably constructed from a flexible material (e.g., an elastomer), such that the electronics housing 144 can conform to a variety of head sizes and shapes. Additionally or alternatively, the electronics housing 144 can be fully or partially rigid (e.g., rigid device constructed to conform to the head of the user, or include a device configured with rigid regions to protect the electronics module separated by flexible regions such as regions where the cross-section of the electronics housing 144 is designed with a decreased second moment to facilitate bending in a certain direction), which can function to add structural support to the device, protect the electronics module, facilitate attachment and detachment of the electrode assembly, or perform any other suitable function. The electronics housing 144 can be constructed from a polymeric material (e.g., elastomer, plastic, silicone, etc.), a foam or sponge, a conductive material (e.g., between the electronics module and the electrode assembly), an insulative material (e.g., to protect a user), or any other material or combination of materials. The electronics housing 144 can include any number of housing support materials (e.g., as shown in FIG. 5C), which can function to physically support any or all of the electronics subsystem 130, retain any or all of the electronics subsystem 130 within a volume of the electronics housing 144, prevent a flexible electronics housing 144 from collapse (e.g., under compression), guide placement of one or more components of the electronics subsystem 130, and/or perform any other suitable function. The housing support material(s) can include any or all of rigid connection substrates, frames, plates, blocks, and/or any other suitable component. One or more housing support materials are preferably constructed from a relatively rigid material (e.g., polymer, plastic, metal, wood, materials having an elastic modulus above 100 MPa, above 1 GPa, above 3 GPa, etc.); additionally or alternatively, one or more housing support materials can be constructed from a relatively flexible and/or compliant material (e.g., polymer, rubber, foam, sponge, felt, fabric, materials having an elastic modulus below 3 GPa, below 2 GPa, below 1 GPa, below 100 MPa, below 10 MPa, etc.).

Preferably, the device includes one electronics housing 144 but can additionally or alternatively include multiple electronics housings 144 (e.g., to spatially distribute the electronics module 120, to optimize placement of one or more components of the electronics module 120, etc.), multiple pieces to a single electronics housing (e.g., an outer elastomeric cover and an inner flexible cover), or any other number and arrangement. The electronics housing 144 can define a volume wherein the electronics subsystem 130 is fully enclosed within the volume, partially enclosed within the volume, or not at all enclosed within the volume. In one variation, the electrode housing 120 serves as at least part of the electronics housing. In an example, for instance, the electronics housing 130 can be arranged within a recess of the electrode housing 120. The electronics housing (e.g., a backing piece) can then be arranged over the recess to enclose the electronics subsystem 130.

In one variation, the electronics housing 144 includes a flexible shell at least partially enclosing the electronics subsystem 130. In a specific example, the flexible shell is constructed from an inner piece connected to an outer piece. The inner and outer pieces can be constructed from the same material or from different materials (e.g., inner piece has higher flexibility than outer piece).

In a second variation, the electronics housing 144 is formed from part or the entirety of the electrode housing 120. In an example, for instance, an outer (e.g., furthest from the user) surface of the electrode housing can form an inner (e.g., closes to the user) surface of the electronics housing 144. In a specific example of this, the electronics subsystem 130 can be at least partially arranged in a recess of the electrode housing 120. In another example, the electrode housing 120 can contain part or all of the electronics subsystem.

3.13 System—Attachment System

The system 100 preferably includes one or more attachment systems 150 configured to connect any or all of the electrode assembly 110 to any or all of the coupler assembly 128 but can additionally or alternatively include any number of attachment systems 150 to connect any element of the system to any other element of the system. The attachment system 150 functions to electrically connect components of the system together but can additionally or alternatively function to mechanically connect components of the system together.

An attachment system 150 preferably includes a first electronic coupling assembly 151 (e.g., a set of conductive polymer contacts) arranged on the electrode housing 120 (e.g., on an outer broad surface of the electrode housing 120) and a second electronic coupling assembly 151 (e.g., conductive polymer body including a set of conductive polymer contacts) arranged on the coupler assembly 128 (e.g., on an inner broad surface of the electronics housing 144 adjacent the outer broad surface of the electrode housing 120), the first electronic coupling assembly configured to be electrically connected and/or mechanically connected the second electronic coupling assembly 151, but one or more electronic coupling assemblies 151 can additionally or alternatively be arranged elsewhere in the system 100. Additionally or alternatively, an electronic coupling assembly 151 can be arranged between an electrode assembly and any other element of the system 100. The attachment system 150 is preferably aligned in a vertical direction, such as along an inferior-superior axis when the device is placed on a user's forehead. This can function to maximize a range of flexibility of the device about this axis. In a variation where the electrodes are placed to the sides of the attachment system 150, for instance, having the attachment system 150 be vertically aligned can enable a greater flexibility about the inferior-superior axis, thereby allowing the electrodes to properly conform to a wide variety of head shapes. Additionally or alternatively, the attachment system can have no single axis of alignment, be horizontally aligned, or arranged/aligned in any other way.

The attachment system 150 (e.g., set of electronic coupling assemblies 151) is preferably at least partially constructed from a conductive material (e.g., conductive polymer such as a conductive rubber or carbon rubber, metal, etc.) to establish an electrical connection between the components. Additionally or alternatively, the attachment system 150 can be at least partially constructed from a non-conductive (e.g., insulative material) or any other material. In one variation, for instance, a non-conductive material (e.g., non-conductive polymer, non-conductive elastomer, etc.) can surround a conductive material (e.g., set of conductive polymer contacts), wherein the non-conductive material can serve as mechanical connector (and/or an alignment tool) and the conductive material can serve as an electrical connecter. In one example of this, the non-conductive material includes a sealing mechanism (e.g., a face seal gasket). In another specific example, a face seal gasket separates the conductive material from the non-conductive material. In some variations, the material(s) of the attachment system can be flexible (e.g., rubber, elastomer, etc.) and/or compliant (e.g., rubber, foam, sponge, etc.) for comfort, conforming to a user's head, etc. In other variations, the material(s) of the attachment system can be rigid (e.g., metallic, magnetic, polymeric, wood, etc.) to contribute structural support or for any other purpose.

The attachment system 150 preferably includes a set of terminals arranged in one or more electronic coupling assemblies 151, wherein each of the terminals is electrically connected to a single electrode 112. Additionally or alternatively, the attachment system can include a single terminal connected to one or more electrodes, multiple terminals connected to a single electrode, or any number and arrangement of terminals and electrodes. In some variations, the set of terminals includes one or more gaskets (e.g., face seal gaskets), which can function to fluidly seal the attachment system 150 from a fluid (e.g., conductive solution), to isolate a terminal from one or more other terminals, or for any other purpose.

In some variations, the attachment system 150 includes a first electronic coupling assembly 151 connected to the electrode assembly 110 and a second electronic coupling assembly 151 connected to the electronics housing 144, wherein the first and second electronic coupling assemblies 151 are removably couplable to each other. In other variations, the first and second attachment pieces can be permanently coupled to each other.

In some variations, the attachment system 150 includes one or more mechanical attachment systems. The mechanical attachment system can be integrated into an electrical attachment system or be separate. The mechanical attachment system 150 can function to connect the electrode housing 120 to the electronics housing 144, the electrode assembly 110 to the electronics subsystem 130, and/or to connect any other components of the system 100. The mechanical attachment system can include a set of attractive (e.g., opposing polarity) magnetic components (e.g., disc magnets, steel plates, etc.), a set of contacts (e.g., male attachment piece) which fit into a set of receptacles (e.g., female attachment piece), a hook-and-loop fastener (e.g., Velcro) system, adhesive, ties, or any other mechanical attachment component. In one example, the electronics housing 144 includes a set of magnets (e.g., disc magnets), which form a mechanical connection with a steel plate in the electrode housing 120.

The attachment system 150 can further include any number of attachment support materials, which can function to structurally support the attachment system 150, such as in the implementation of an attachment system 150 in a flexible/compliant structure (e.g., flexible electronics housing). This can include one or more rigid connection blocks, plates, rods, etc. In one variation, as shown in FIG. 7C, the attachment system 150 can include a set of connection blocks (e.g., an inner connection block and an outer connection block) proximal one or more other components of the attachment system 150, such as a magnetic mechanical attachment system 150. In some variations, the attachment support materials can include any or all of the housing support materials.

Figure 6A:
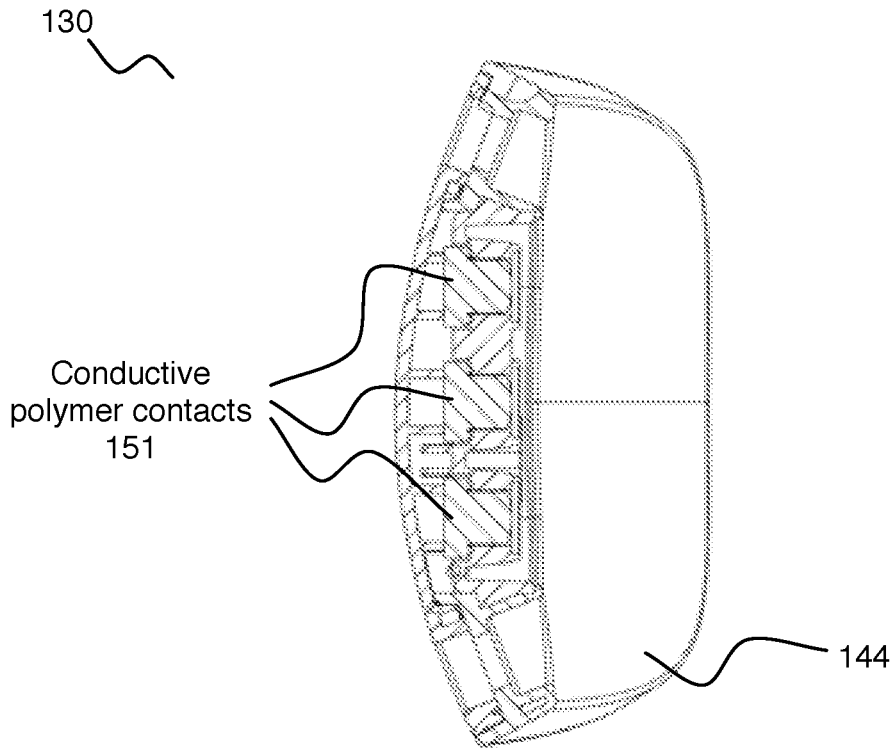
FIG. 6A depicts a cross-sectional view of a variation of a coupler assembly having an attachment system including a set of conductive polymer contacts.
Figure 6B:
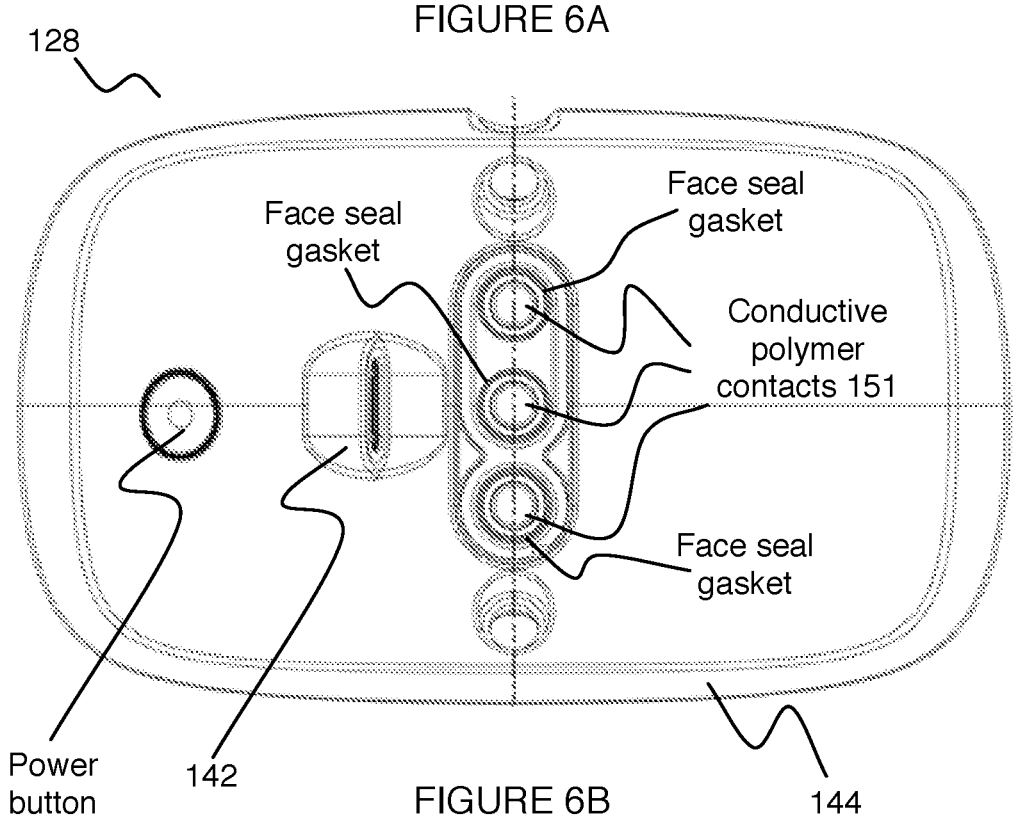
FIG. 6B depicts a view of a variation of a coupler assembly having an attachment system including a set of conductive polymer contacts.

In one variation, one or more electronic coupling assemblies 151 of the attachment system 150 includes one or more conductive polymer (e.g., conductive rubber such as carbon rubber) bodies. In a specific example, an electronic coupling assembly including a conductive polymer body is exposed through an opening of the electronics housing 144, wherein the conductive polymer body can include a set of conductive polymer contacts (e.g., as shown in FIGS. 6A-6B) which couple with an electronic coupling assembly 151 including a complementary set of conductive polymer contacts (e.g., conductive polymer receptacles on an outer surface of the electrode housing 120, as shown in FIGS. 7D-7E). In another specific example, the electronic coupling assembly 151 of the electrode assembly 120 includes a set of conductive polymer contacts which are couplable to a complementary set of conductive polymer contacts (e.g., conductive polymer receptacles) of an electronic coupling assembly 151 of the electronics housing 144. Preferably the complementary sets of conductive polymer contacts are vertically aligned (e.g., FIGS. 6A-6B and 7D-7E) but can additionally be arranged in any other way. The conductive polymer contacts can be arranged with a fixed spacing, a variable spacing, or any other spacing. In one example, a set conductive polymer contacts are evenly spaced. In another example, the spacing between a first and second conductive polymer contact is smaller than the spacing between a second and third conductive polymer contact. The attachment system can include any number of contacts/receptacles (e.g., one per electrode, one per electrode plus an additional contact, etc.). This variation can further include one or more sealing mechanisms arranged between complementary rubber contacts to prevent fluid ingress into a volume (e.g., cavity, barrel, etc.) of an electronic coupling assembly 151 and/or between electronic coupling assemblies 151.

In another variation, the attachment system includes a conductive polymer (e.g., carbon rubber) attachment system along with a mechanical attachment system (e.g., magnetic attachment system).

In yet another variation, the attachment system includes a first electronic coupling assembly 151 having a set of non-polymeric (e.g., metallic) contacts which are couplable with a second electronic coupling assembly 151 having a set of non-polymeric (e.g., metallic) receptacles. Additionally or alternatively, one electronic coupling assembly 151 having a conductive polymeric material (e.g., conductive rubber) can be coupled to an electronic coupling assembly 151 having a conductive non-polymeric material (e.g., metal).

3.14 System—Sealing Structures

The system 100 preferably includes one or more sealing structures, wherein a sealing structure can function to obstruct liquid (e.g., conductive gel or liquid, user perspiration, spills, rain, water from washing, etc.) access to the electronics subsystem (e.g., during use). The sealing structure can include any or all of a sealing component (e.g., gasket, O-ring, stopper, etc.) and/or an interface between components (e.g., adhesive interface, laminated interface, interlocking interface, press-fit interface, etc.) formed by any form of manufacture and/or assembly (e.g., lamination, injection molding, co-molding, press-fitting, etc.). Preferably, an attachment system 150 between the electrode assembly 110 and the electronics subsystem 130 includes a sealing structure; additionally or alternatively, a sealing structure (e.g., face-seal gasket arranged on the perimeter of one or more electrodes 112) is arranged between one or more electrodes 112 and the rest of the electrode assembly 110, between an attachment system 150 and the electronics subsystem 130, between the electronics housing 144 and any other element of the electronics subsystem 130, and/or between any other elements of the system 100.

In one variation, two or more elements of the system 100 collectively define the sealing structure. In a specific example, for instance, the attachment system 150 (e.g., conductive polymer body of the electronics subsystem 130 and electronic coupling assembly of the electrode assembly 110) and the electronics housing 144 collectively define a sealing structure.

Figure 7A:
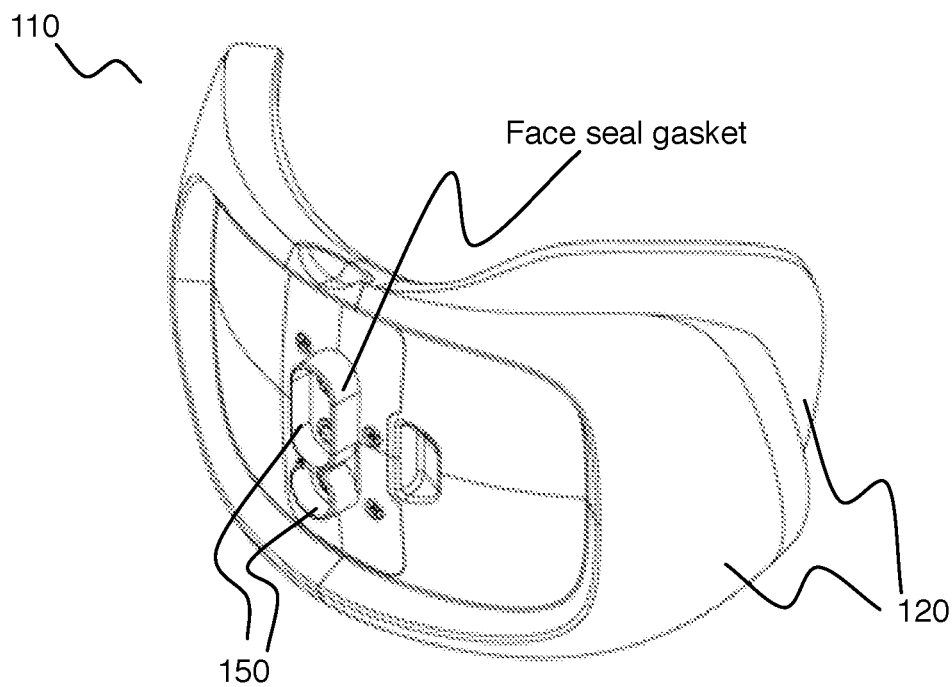
FIG. 7A depicts a view of a variation of an electrode assembly.
Figure 7B:
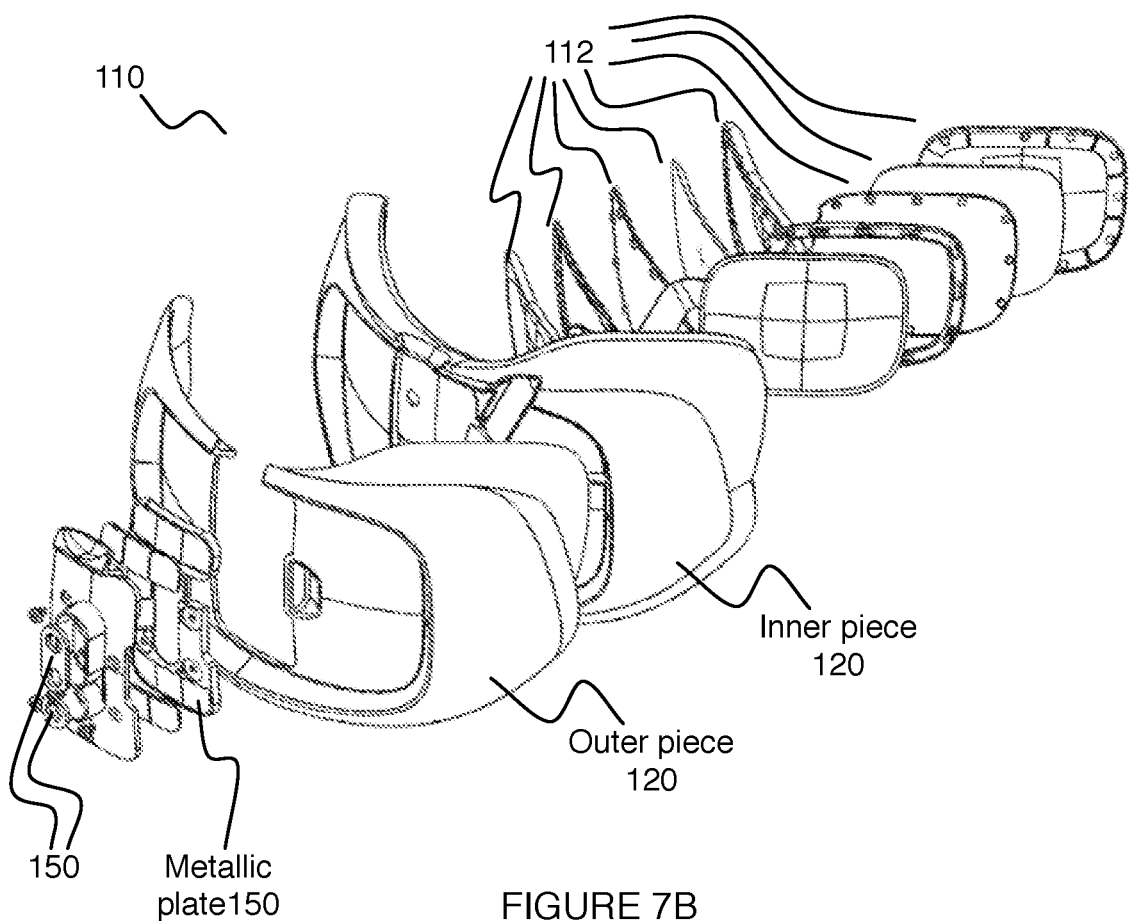
FIG. 7B-7C depict exploded views of a variation of an electrode assembly.
Figure 7C:
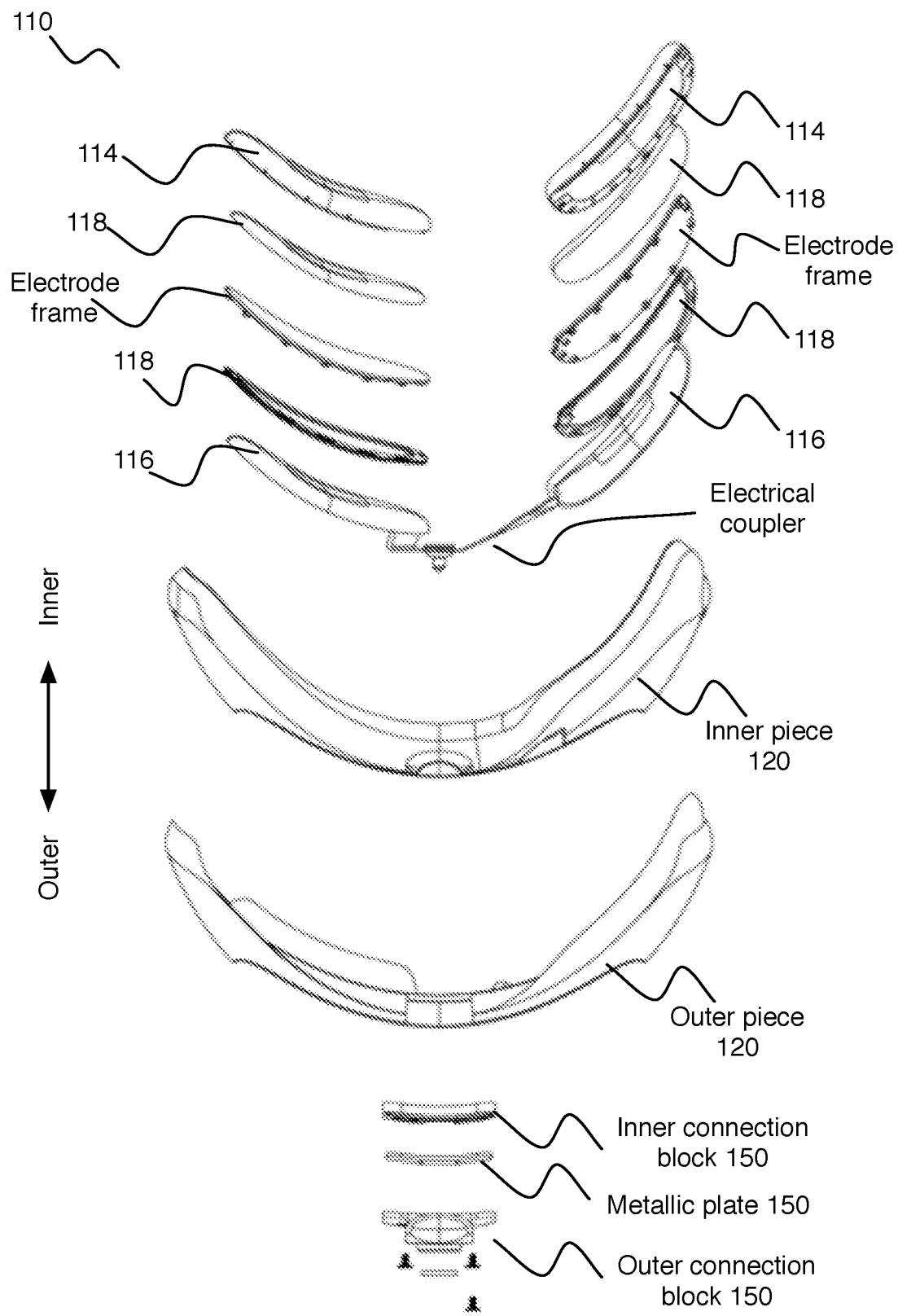
Figure 7D:
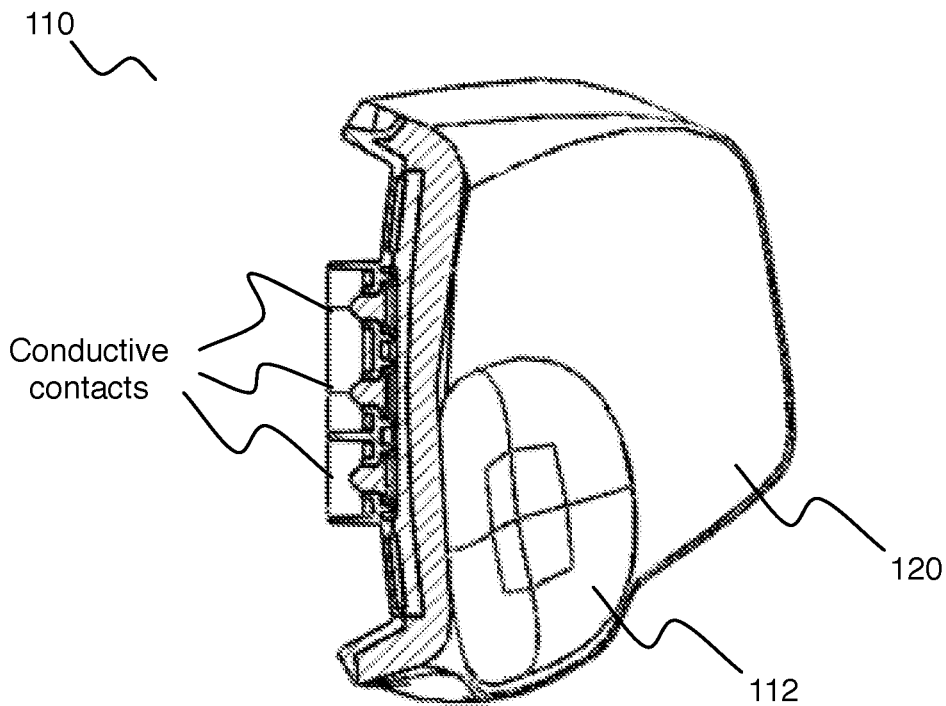
FIG. 7D depicts a cross-sectional view of an electrode assembly having an attachment system including a set of conductive polymer contacts.
Figure 7E:
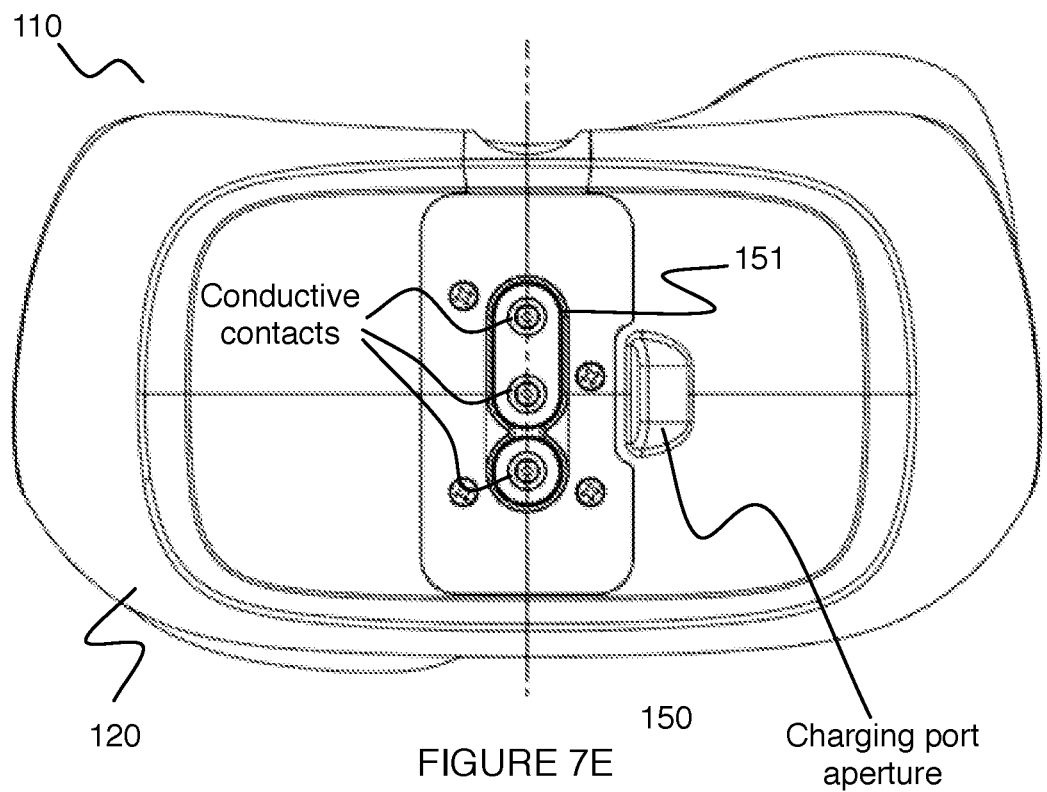
FIGS. 7E and 7F depict views of an outer broad surface and an inner broad surface, respectively, of a variation of an electrode assembly.
Figure 7F:
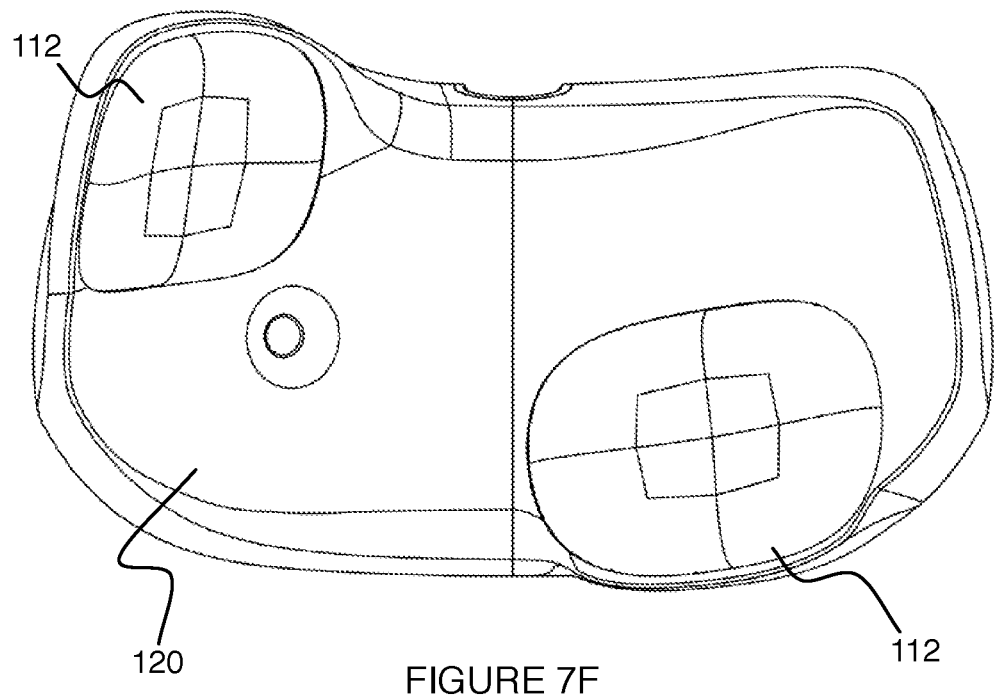

In a second variation (e.g., as shown in FIG. 7A), the sealing structure is formed from one or more face seal gaskets incorporated with (e.g., surrounding) an electrical attachment system 150. The one or more face seal gaskets are preferably constructed from an elastomeric material but can additionally or alternatively be constructed from any polymeric material and/or any other material. The one or more face seal gaskets are preferably constructed from a non-conductive material (e.g., non-conductive elastomer) but can additionally or alternatively be constructed from a conductive material. In a specific example, a face seal gasket surrounds a set of conductive polymer contacts. In a specific example (e.g., as shown in FIG. 6B), a face seal gasket surrounds each of a set of contacts (e.g., the set of conductive polymer contacts arranged on the coupler assembly, the set of conductive polymer contacts arranged on the electrode assembly, both sets of conductive polymer contacts, etc.). In yet another specific example, a first face seal gasket can be arranged around a set of conductive polymer contacts (e.g., conductive rubber contacts) and an additional set of face seal gaskets can be arranged around each of a set of conductive polymer contacts.

In a third variation, one or more conductive polymer contacts is constructed with a feature to prevent fluid ingress. In a first specific example, one or more conductive polymer contacts are configured to be press fit together to prevent fluid ingress. In a second specific example, one or more conductive polymer contacts includes a surface texture for a sealed fit when mated with another conductive polymer contact. In a third specific example, one or more conductive polymer contacts include a gasket, rim, and/or other features for establishing a seal when mated with another element (e.g., complementary conductive polymer contact) of the electronic coupling assembly 151.

3.15 System—Head Apparel Assembly

The system 100 preferably includes a head apparel assembly 170, which functions to secure the system 100 (e.g., a cosmetic outer element 160, one or more electrodes 112, etc.) to a head region (e.g., forehead) of the user. Additionally or alternatively, the system 100 can be secured to a head region of the user using an adhesive, a sticky conductive solution, through gravity, using an external head apparel assembly (e.g., a hat of a user), or using any other element.

The head apparel assembly 170 is preferably adjustable and/or elastic in order to fit a variety of user head morphologies but can alternatively be a single size. The head apparel assembly 170 can include a compliant material (e.g., foam helmet), a flexible material (e.g., an elastic strap), a rigid material (e.g., a polymer frame, glasses frame/glasses arms, headphone/headset frame, etc.), a fabric material (e.g., polyester band, hat, etc.), any other material or any combination of materials. The head apparel assembly 170 can include any or all of: a strap (e.g., elastic strap), helmet (e.g., foam helmet, biking helmet, football helmet, etc.), frame (e.g., glasses frame, headphone/headset frame, polymer frame, etc.), headband (e.g., sweatband), hat (e.g., baseball cap, beanie, etc.), and/or any other element.

The head apparel assembly can be connected to the electrode assembly 110, the electronics subsystem 130, any other element of the system 100, held to a user's head through compression, or not attached at all. The head apparel assembly can be attached to the rest of the system 100 with any type and number of fasteners, such as screws, press-fit components (e.g., press-fit bollards), adhesive, hook-and-loop fasteners, ties, buttons, snaps, straps, buckles (e.g., watch strap buckle), clamps, and/or any other suitable fastening mechanism.

3.16 System—Cosmetic Outer Element

In some variations, the head apparel assembly 170 includes a cosmetic outer element 160 (e.g., FIGS. 4A-4E), which functions to contribute structural stability to the system 100 and/or provide an attractive cosmetic appearance to the system 100. Additionally or alternatively, the cosmetic outer element 160 can function to retain the system 100 to the head of a user, hold the system 100 in place in a predetermined location (e.g., proximal a set electrode placement regions), protect any part of the system 100 (e.g., the electronics subsystem) from the environment and/or wear-and-tear, and/or perform any other suitable function.

The cosmetic outer element 160 is preferably connected to one or more other components of the head apparel assembly 170 (e.g., elastic strap, hat, headset, headphones, flexible frame arranged circumferentially around the user), such that the cosmetic outer element 160 is retained at a desired location on the head (e.g., over the forehead region) of a user. Additionally or alternatively, the cosmetic outer element 160 can be secured to the head of a user (e.g., with an adhesive) without additional components of the head apparel assembly 170, held with compression, held at a distance (e.g., with a frame), or otherwise arranged proximal the head of a user. The cosmetic outer element 160 is preferably arranged further away from the user (e.g., more external than another element of the system 100, etc.) than the electrode assembly 110, but can additionally or alternatively be arranged partially external the electrode assembly 110, partially or fully external the electronics subsystem 130, or arranged in any other way with respect to the system 100.

The cosmetic outer element 160 is preferably constructed with a similar shape (e.g., curvature, set of contours, depth, profile, etc.) as one or more components of the system 100 arranged closer to the user than (e.g., internal) the cosmetic outer element 160, such that the cosmetic outer element 160 can be stacked on/layered over the inner component(s). Additionally or alternatively, part or all of the cosmetic outer element 160 can be constructed with a similar shape (e.g., curvature, set of contours, depth, profile, etc.) as that of a head region (e.g., forehead, neck) of the user, to facilitate and maintain proper placement of any or all of the system 100 on a user. Further additionally or alternatively, the cosmetic outer element 160 can be compliant and/or flexible enough to take on a wide range of shapes, can be constructed with a different shape than any other component of the electrostimulation device, or can be constructed to have any other suitable geometry.

A broad surface (e.g., outer surface, inner surface) of the cosmetic outer element 160 can generally be the same size (e.g., average size among a sample of users, largest size in a sample of users, etc.) as a forehead region, one or more electrode regions, a brain/scalp region, any other region of the user, or can be any suitable size.

The cosmetic outer element 160 is preferably constructed from one or more comfort materials, such as, but not limited to: relatively compliant materials (e.g., elastic modulus less than 100 MPa) and/or relatively flexible materials (e.g., spring constant less than 200 N/m, less than 100 N/m, less than 50 N/m, less than 30 N/m, between 20 and 80 N/m, etc.) in order to contour/conform to a variety of user head morphologies, but can additionally or alternatively be constructed from one or more support materials (e.g., rigid materials, materials having an elastic modulus above 100 MPa, above 1 GPa, above 3 GPa, etc.), a combination of comfort and support materials, or any other material or combination of materials. The cosmetic outer element 160 is preferably insulative (e.g., to protect a user), but can additionally or alternatively be conductive. In some variations, the cosmetic outer element 160 is hydrophobic, such that the cosmetic outer element does not absorb liquids (e.g., from user perspiration, from the environment, from a conductive solution, etc.), but can additionally or alternatively be hydrophobic.

In preferred variations, the cosmetic outer element 160 includes one or more cosmetic support materials, such as a frame, plate, lattice, beam, or any other component which functions to support (e.g., maintain) the structure of the cosmetic outer element 160. The cosmetic support material(s) can be constructed from a polymer, metal, rigid foam or sponge, or any other material(s). The cosmetic outer element 160 can further include one or more compliant and/or flexible materials, such as a foam pad, polymeric plate, felt pad, sponge layer, fabric, or any other material. In some variations, a compliant material is arranged closest to the user for comfort and a rigid material is arranged external to the compliant material for protection of the system 100. The compliant material(s) can be constructed from a foam or sponge, fabric (e.g., felt, polyester, cotton, etc.), polymer (e.g., silicone, rubber, etc.) or any other material(s). The support material(s) and the compliant/flexible material(s) can be layered (e.g., in an alternating fashion), partially or fully surrounded by (e.g., wrapped in) a fabric backing, and/or arranged in any other way.

There is preferably one cosmetic outer element 160 for each head apparel assembly 170, but the head apparel assembly 170 can additionally or alternatively include multiple cosmetic outer elements 160 (e.g., one per electrode, multiple per electrode, etc.) or no cosmetic outer element 160.

The cosmetic outer element 160 preferably includes one or more attachment sites for one or more other components (e.g., strap, frame, etc.) of the head apparel assembly 170. The attachment site(s) can include any or all of: one or more cutout regions (e.g., to attach the ends of a strap), recesses or grooves (e.g., to retain and/or guide placement of a strap), hinges (e.g., to attach arms of glasses), hooks, clasps, hook-and-loop fasteners (e.g., Velcro), adhesives, clamps, or any other type of fastener or means for attachment. Additionally or alternatively, the cosmetic outer element 160 can serve as the head apparel assembly (e.g., wrap circumferentially around the head of a user).

In a first variation, the cosmetic outer element 160 is arranged external to the electrode assembly 110 and the electronics subsystem 130. In a first specific example, the cosmetic outer element 160, electrode housing 120, and electronics housing 144 are all constructed to have a size and curvature similar to those of a user's forehead region, such that the components can be stacked/layered over each other and secured to the user's forehead. The cosmetic outer element 160 in this specific example can further include an external and/or an internal fabric layer, which can function to add comfort to the device, conceal one or more materials (e.g., rigid frame of the cosmetic outer element) of the device, and/or contribute to the aesthetic qualities of the device.

In a second variation, the cosmetic outer element can function to connect one or more electrodes 112 to a head apparel assembly. In a specific example, as shown in FIG. 10, the cosmetic outer element 160 can include multiple pieces, each arranged on a broad outer surface of an electrode.

Figure 10:
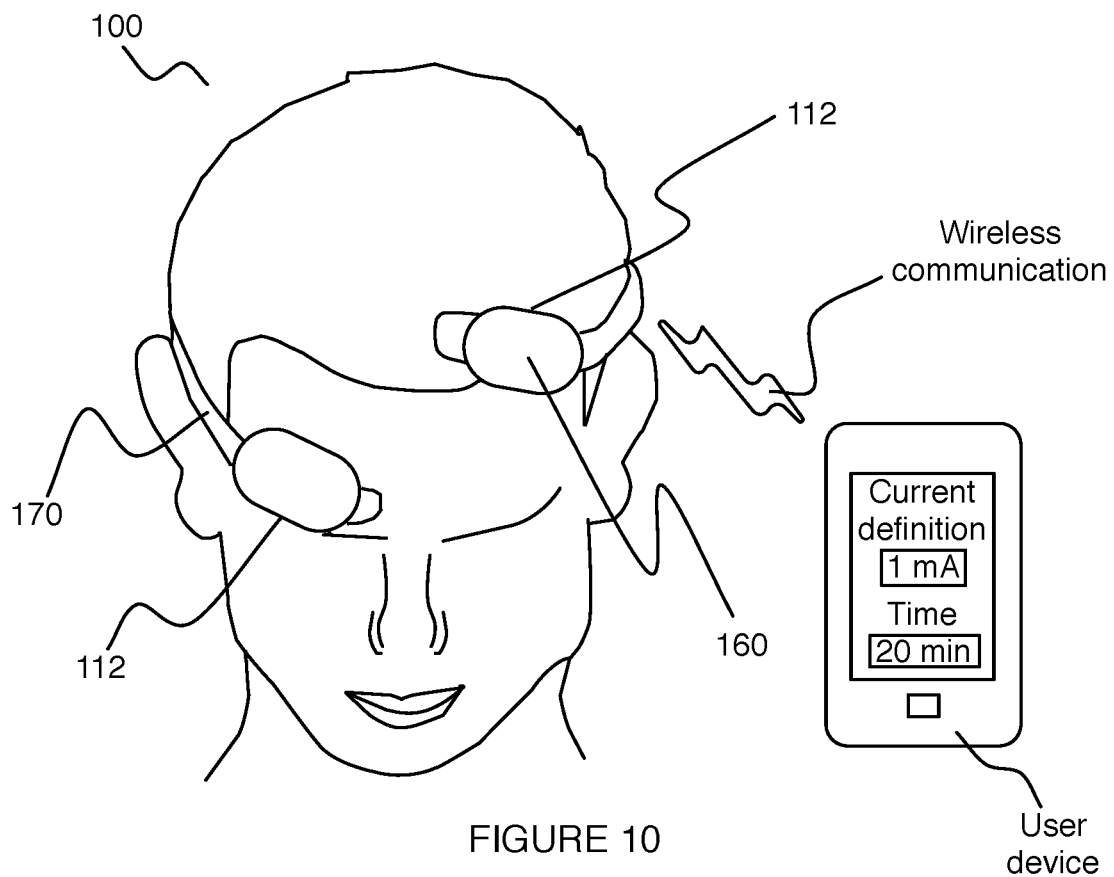
FIG. 10 depicts a variation of a system for providing electrical stimulation and/or detecting biosignals of a user having a head assembly mechanism including a frame wrapped at least partially circumferentially around the head of a user.
Figure 11:
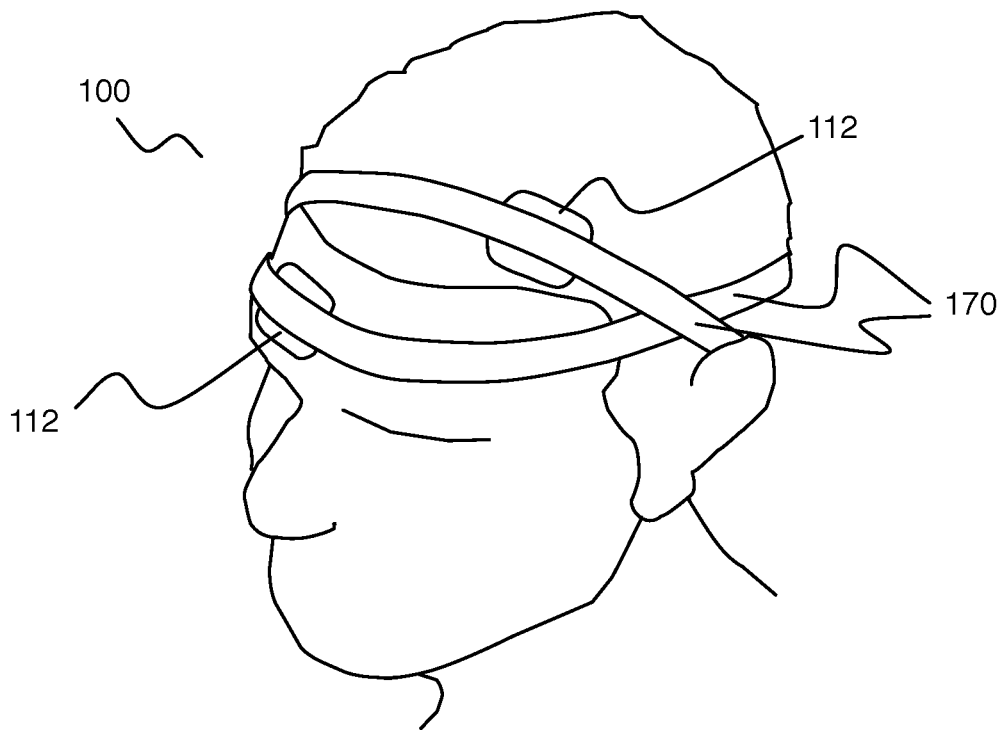
FIG. 11 depicts a variation of a system for providing electrical stimulation and/or detecting biosignals of a user having a head assembly mechanism including a set of bands wrapped at least partially circumferentially around the head of a user.
Figure 12:
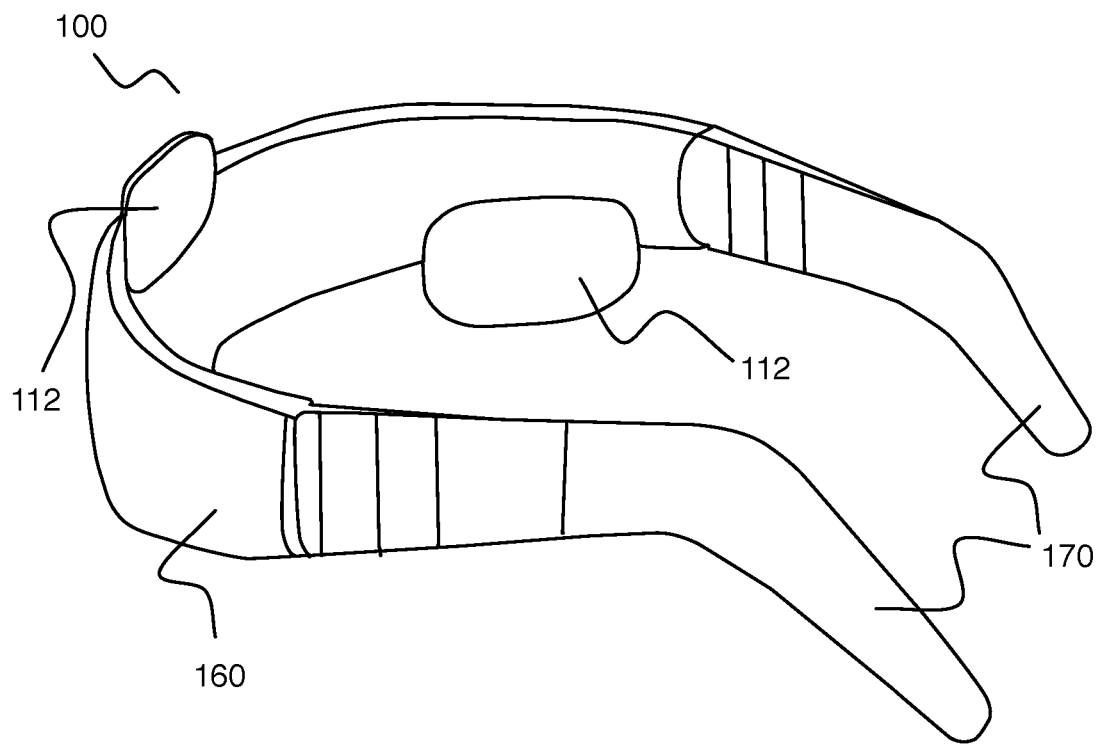
FIG. 12 depicts a variation of a system for providing electrical stimulation and/or detecting biosignals of a user having a head assembly mechanism including a glasses frame.

In a third variation (e.g., as shown in FIGS. 10-12) the head apparel assembly 170 includes a cosmetic outer element 160 connected to a frame arranged at least partially circumferentially around the head of a user. In a first specific example, the cosmetic outer element 160 is connected to a pair of glasses arms, the glasses arms resting on a user's ears, wherein the glasses arms function to couple the cosmetic outer 160 to a user's head (e.g., forehead region).

In a fourth variation, the cosmetic outer element 160 has a layered structure including a curved plate (e.g., plastic plate) arranged externally (e.g., further from the user) and a foam pad arranged internal (e.g., closer to the user) to the curved plate. In a specific example, the cosmetic outer element 160 is wrapped in a fabric layer. Any or all of the cosmetic outer element 160 layers can be secured together through a lamination process, using adhesive, press-fit bollards, screws, a snap ring, or in any other way with any suitable component of the system 100.

In a fifth variation, the system 100 is in the form of a headband, wherein the head apparel assembly includes an elastic strap. In a first example, the strap is connected to a cosmetic outer element 160, wherein the cosmetic outer element 160 is placed on the forehead of a user and the strap is arranged around the back of the user's neck or head. In a second example, the strap runs circumferentially around the head of a user and can be arranged external to the system 100, within a recess of the cosmetic outer 160, between a cosmetic outer 160 and an electronics subsystem 130, between an electronics subsystem 130 and an electrode assembly 120, or arranged in any other way.

Figure 13:
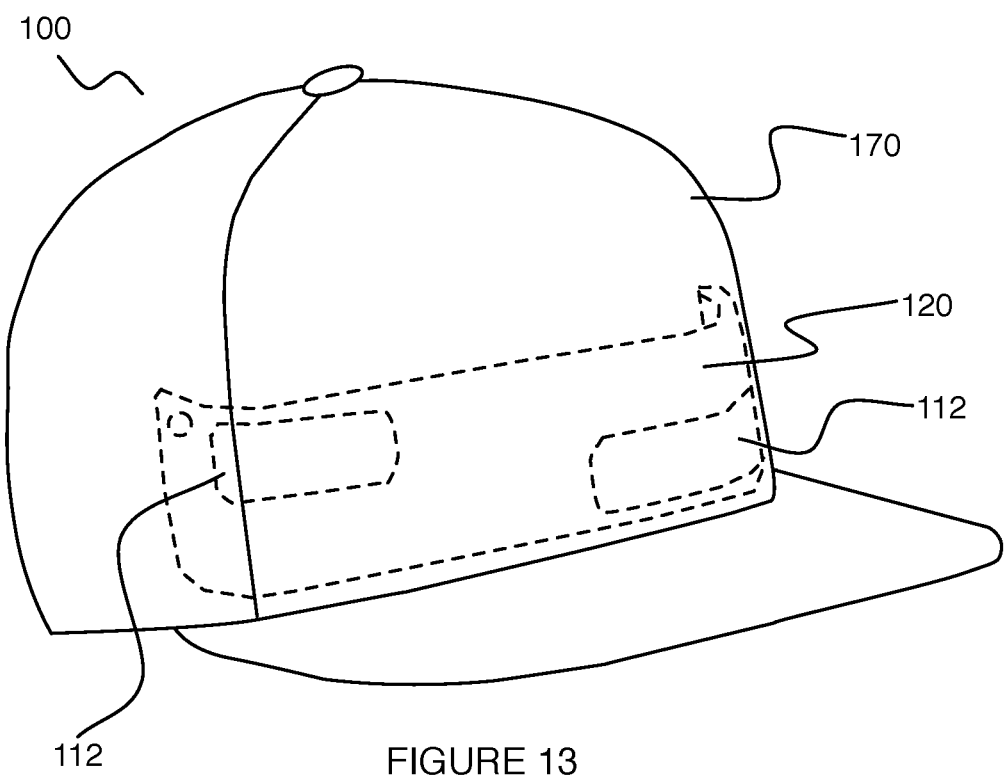
FIG. 13 depicts a variation of a system for providing electrical stimulation and/or detecting biosignals of a user having a head assembly mechanism including an electrode assembly insertable into a hat.

In a sixth variation (e.g., as shown in FIG. 13), the system 100 is in the form of a hat insert, wherein the head apparel assembly 170 includes a hat. In a specific example, the hydrophilic layer 114 of one or more electrodes 112 includes a set of ridges to part through a user's hair in order to establish contact between the electrode 112 and the user's scalp. In another specific example the system 100 can include an attachment system 150 (e.g., hook, Velcro, adhesive, etc.) to connect the system 100 to the hat. In a third variation, the system 100 is simply held by compressive forces from the hat.

In a seventh variation (e.g., as shown in FIGS. 10-12), the system 100 is in the form of a frame, wherein the frame at least partially circumferentially wraps around the head of the user to secure the system 100 to the user's head. In a first specific example (e.g., as shown in FIG. 12), the frame includes a glasses frame (e.g., set of rigid glasses arms). In a second specific example, the frame is bendable such that the user can adjust the configuration of the frame to fit the user and target a desired set of stimulation regions. In a third variation, the frame is rigid (e.g., constructed based on a set of user head measurements). In a fourth variation, the frame is elastic to deform elastically to accommodate head size and shape variation.

Although omitted for conciseness, the preferred embodiments include every combination and permutation of the various system components.

As a person skilled in the art will recognize from the previous detailed description and from the figures and claims, modifications and changes can be made to the preferred embodiments of the invention without departing from the scope of this invention defined in the following claims.

We claim:

1. A system for electrically stimulating a user, the system comprising:
   a pair of electrodes comprising a first electrode and a second electrode;
   a compliant base configured to flex about an inferior-superior axis and conform to a curvature of a forehead region of the user during use of the system, the compliant base retaining each of the pair of electrodes in position and separating each of the pair of electrodes from each other according to a set of arrangements, wherein each of the set of arrangements defines:
      an angle between a first axis of the first electrode and a second axis of the second electrode, the first axis being perpendicular to an inner broad surface of the first electrode and extending through a center point of the inner broad surface of the first electrode, the second axis being perpendicular to an inner broad surface of the second electrode and extending through a center point of the inner broad surface of the second electrode, wherein the angle is defined based on a projection of the first and second axes in a transverse plane and has a value between 36.5 and 116.5 degrees; and
      a horizontal spacing between the center point of the inner broad surface of the first electrode and the center point of the inner broad surface of the second electrode, the horizontal spacing defined along a medial-lateral axis perpendicular to the transverse plane, wherein the horizontal spacing has a value between 54 and 104 millimeters; and
   an electronics subsystem.

2. The system of claim 1, wherein the first electrode is configured to be arranged proximal to a right hemispheric brain region and wherein the second electrode is configured to be arranged proximal to a left hemispheric brain region.

3. The system of claim 1, wherein each of the pair of electrodes comprises:
   a hydrophilic pad; and
   a support structure retaining the hydrophilic pad.

4. The system of claim 3, wherein each of the pair of electrodes further comprises:
   a conductive polymer substrate in contact with the hydrophilic pad; and
   an electrical coupler.

5. The system of claim 1, further comprising an electronic coupling assembly coupled to each of the pair of electrodes and arranged at least partially through the compliant base, the electronic coupling assembly configured to couple the pair of electrodes to the electronics subsystem.

6. The system of claim 5, wherein the electronic coupling assembly comprises a conductive polymer frame connected to a first conductive polymer substrate of the first electrode and to a second conductive polymer substrate of the second electrode, wherein the first and second electrodes are electrically connected through the conductive polymer frame.

7. The system of claim 6, wherein the first and second electrodes are further mechanically connected through the conductive polymer frame.

8. The system of claim 5, wherein the electronic coupling assembly comprises a first set of conductive polymer contacts and wherein the electronics subsystem comprises a second set of conductive polymer contacts, wherein the first and second sets of conductive polymer contacts are removably coupleable.

9. The system of claim 8, wherein each of the first and second sets of conductive polymer contacts is a carbon rubber contact.

10. The system of claim 1, wherein the compliant base comprises a hydrophobic material.

11. The system of claim 1, wherein the set of arrangements comprises multiple arrangements.

12. A system for electrically stimulating a user, the system comprising:
    a pair of electrodes comprising a first electrode and a second electrode, wherein each of the first and second electrodes comprises a conductive polymer substrate in contact with a hydrophilic pad;
    a compliant base configured to flex about an inferior-superior axis and conform to a curvature of a forehead region of the user during use of the system, the compliant base retaining each of the pair of electrodes in position and separating each of the pair of electrodes from each other according to a set of arrangements, wherein each of the set of arrangements defines:
        an angle between a first axis of the first electrode and a second axis of the second electrode, the first axis being perpendicular to an inner broad surface of the first electrode and extending through a center point of the inner broad surface of the first electrode, the second axis being perpendicular to an inner broad surface of the second electrode and extending through a center point of the inner broad surface of the second electrode, wherein the angle is defined based on a projection of the first and second axes in a transverse plane and has a value between 36.5 and 116.5 degrees;
    a housing defining an internal volume;
    an electronics subsystem arranged within the internal volume; and
    an electronic coupling assembly coupled to each of the set of electrodes and arranged at least partially through the compliant base, the electronic coupling assembly configured to couple the set of electrodes to the electronics subsystem.

13. The system of claim 12, wherein the electronic coupling assembly comprises:
    a conductive polymer frame connected to a first conductive polymer substrate of the first electrode and to a second conductive polymer substrate of the second electrode.

14. The system of claim 12, wherein the housing is configured to flex about the inferior-superior axis.

15. The system of claim 12, wherein each of the set of arrangements further defines a horizontal spacing between a center point of the inner broad surface of the first electrode and a center point of the inner broad surface of the second electrode, the horizontal spacing defined along a medial-lateral axis perpendicular to the transverse plane, wherein the horizontal spacing has a value between 54 and 104 millimeters.

16. The system of claim 12, wherein the set of arrangements comprises multiple arrangements.

17. The system of claim 12, wherein the hydrophilic pad is a hydrophilic foam.

18. The system of claim 17, wherein each of the first and second electrodes further comprises:
    a support structure retaining the hydrophilic foam; and
    an electrical coupler.

19. The system of claim 12, wherein the electronic coupling assembly comprises a first set of conductive polymer contacts and wherein the electronics subsystem comprises a second set of conductive polymer contacts, wherein the first and second sets of conductive polymer contacts are removably coupleable.

20. The system of claim 12, wherein the electronics subsystem comprises a current source comprising a battery, wherein the system further comprises a charging port electrically connected to the battery and arranged on an internal surface of the housing.

* * * * *